United States Patent [19]

De Paulis et al.

[11] Patent Number: 5,480,631

[45] Date of Patent: * Jan. 2, 1996

[54] RADIOIODINATED BENZAMINES AND METHOD OF THEIR USE AS RADIOIMAGING

[75] Inventors: Tomas De Paulis; Robert M. Kessler; Howard E. Smith, all of Nashville; Aaron Janowski, Portland; Jeffrey A. Clanton, Nashville, all of Tenn.

[73] Assignee: Vanderbilt University, Nashville, Tenn.

[ * ] Notice: The portion of the term of this patent subsequent to Oct. 13, 2099, has been disclaimed.

[21] Appl. No.: 889,646

[22] Filed: May 28, 1992

Related U.S. Application Data

[63] Continuation-in-part of Ser. No. 708,110, May 28, 1991, Pat. No. 5,154,913, which is a continuation of Ser. No. 604,370, Oct. 26, 1990, abandoned, which is a continuation of Ser. No. 122,390, Nov. 19, 1987, abandoned.

[51] Int. Cl.$^6$ .......................... A61K 51/04; A61K 31/40; C07D 207/08; A01N 43/36
[52] U.S. Cl. .......................... 424/185; 514/359; 514/428; 548/567
[58] Field of Search ..................................... 424/1.1, 1.85; 548/567; 514/359, 428

[56] References Cited

PUBLICATIONS

Crawley et al. "Abstract 145 Dopamine Receptors in the Human Brain Imaged w/ a New Ligand Labelled with $^{123}$I", *Clin. Sci.* 70, Suppl. 13 (1986).
Kung et al., "Preparation & Radiolabelling of IBZM: A Potential D-Z Specific Brain Imaging Agent for SPECT", *J. of Labelled Compounds & Radio–Pharmaceuticals*, 23:10–12, Oct., 1986, pp. 1318–1319.

*Primary Examiner*—Gary L. Geist
*Assistant Examiner*—Lara E. Chapman
*Attorney, Agent, or Firm*—Reising, Ethington, Barnard and Perry

[57] ABSTRACT

Novel, substituted benzamides in radioiodinated form are useful in radiopharmaceutical compositions in nuclear medicine as imaging agents to detect, visualize, and analyze the distribution and function of the dopamine D2 receptor in the mammalian brain. These compounds have a specific combination of lipophilicity and dopamine D2 receptor affinity required to attain a required image contrast. The iodinated benzamides identified by the above discovery can be made by reacting a trialkyltin substituted benzamide with an acid in the presence of radioactive iodine which, in turn, is generated by in situ oxidation of an appropriate iodide nuclide salt.

8 Claims, 10 Drawing Sheets

RADIOIODINATED BENZAMINES AND METHOD OF THEIR USE AS RADIOIMAGING

This application is a continuation-in-part of Ser. No. 708,110, filed May 28, 1991, which issued as U.S. Pat. No. 5,154,913 on Oct. 13, 1992, which is a continuation of Ser. No. 604,370, filed Oct. 26, 1990, now abandoned, which is a continuation of Ser. No. 122,390, filed Nov. 19, 1987, now abandoned.

TECHNICAL FIELD

The present invention relates to the selection of optimized radiolabelled compounds for use in clinical nuclear medicine and their method of preparation. More specifically, the present invention relates to both the discovery of the criteria for the selection of optimized compounds for receptor imaging and to the preparation of the radioiodinated form that can be used in a radiopharmaceutical composition as an imaging agent, particularly for the brain.

BACKGROUND OF THE INVENTION

Radiolabelled compounds which are subject to localization in particular organs or tumors therein are of great value for diagnosis of diseases of the human body. For example, thallium 201 and fatty acids labelled with carbon-11 and iodine-123 have been utilized as heart imaging agents. Also, various phosphorate ligands labelled with technetium-99m have been used to image infarcted regions of the heart. Although many useful radiolabelled compounds are known, there remains a need for the discovery of improved compounds which are effective for routine imaging of the brain. In particular, there remains a need for radiolabelled compounds which are useful in imaging dopamine D2 receptors in the brain.

A dopamine D2 ligand for single photon emission tomography (SPECT) imaging would ideally have great selectivity and high affinity for the D2 receptor, low nonspecific binding, and adequate brain uptake for imaging. The in vivo striatal:cerebellar ratios for [$^{11}$C]raclopride and [$^{123}$I]IBM have been reported as 4:1(1) and 2:1(2), respectively, in man. The striatum to cerebellar uptake ratio is representative of an agent's ability to differentiate areas of high and low dopamine D2 receptors occurring outside the striatum. These extrastriatal dopamine D2 receptors, in mesolimbic and mesocortical brain regions, have been postulated to be involved in the pathophysiology of schizophrenia and to be the site of action of neuroleptic drugs. While hypothesis remains controversial, studies of these receptors are difficult because radiolabelled dopamine D2 receptor ligands available by previous art are not adequate for studying limbic and cortical D2 receptors. The reasons for this are related to the comparatively low numbers of D2 receptors and the relatively high concentrations of other receptors, e.g., serotonergic and nonadrenergic in many of these regions.

Substituted benzamides such as sulpiride, raclopride, and IBZM are dopamine D2 specific ligands, but have only moderate affinity for the dopamine D2 receptor, rendering reliable in vivo and in vitro studies of extrastriatal D2 receptors using these ligands impossible. Other substituted benzamides of prior art such as eticlopride, emonapride (YM-09151-2) and spectramide have been reported to be selective and are very potent dopamine D2 ligands. However, while their receptor affinities may be adequate, [$K_D$ 90 pM, 57 pM, and 25 pM respectively], eticlopride and emonapride are very lipophilic(5). This results in moderate to high levels of nonspecific binding to lipids in the brain, which has a significant adverse effect on image contrast. Spectramide, which is structurally related to emonapride and therefore quite lipophilic, also shows relatively high nonspecific binding both in vitro and in vivo in rat brain.

Spiperone and its derivatives have very high affinity for the dopamine D2 receptor, but spiperone's high affinity for the serotonin type 2 receptor severely limits its use for studying cortical and limbic dopamine D2 receptors.

PRIOR ART

Previously disclosed radioiodinated dopamine D2 ligands include a Japanese Patent application 59112971 which discloses an agent, 2-ISP, for dopamine receptors having the following structure:

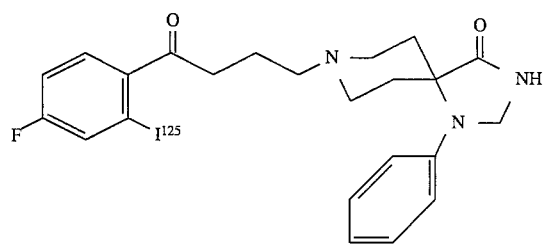

2-ISP is more selective than spiperone for the dopamine D2 receptor, but displays only moderate striatum-to-cerebellum ratio in the mouse brain.

Landwater (J. Label Comp. Radiopharm. 22, 2738, 1985) disclosed a compound, 4-ISP, which is described as a high affinity dopamine receptor probe.

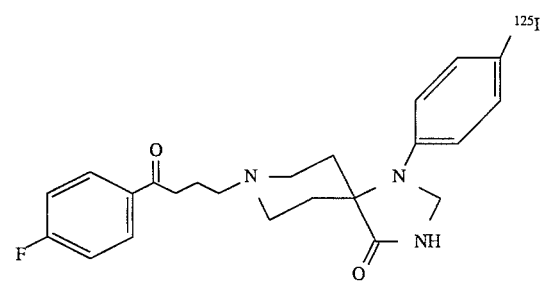

Crawley, F. C. W. et al. Clin. Sci. 70:Suppl. 13, Abstr. 145 (1986), and independently, Kung, H. F. et al. J. Label Comp, Radiopharm. 23:131–1319 (1986) disclose the following compound of Kung IBZM, which is described as an agent for the study of dopamine D2 receptors(7) in vivo:

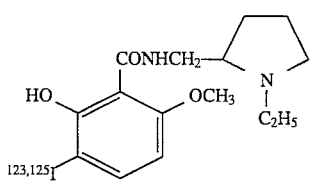

The above compound, having a non-radioactive isotope of iodine, was disclosed in European Patent Application EP 60235. It has a peak striatal:cerebellar ratio in man of only 1.6 to 1.8.

Neumeyer, J. L. et al. *J. Med. Chem.* 28, 729 (1985), discloses the following compound, which is described to have receptor binding behavior similar to that of haloperidol:

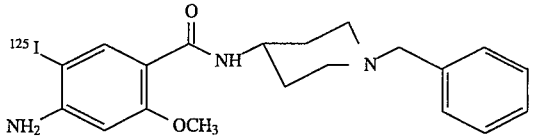

Wilson, A. A. et al. *J. Nucl. Med.* 28, 729 (1987), discloses the following compound which is described to bind to brain receptors blockable by haloperidol:

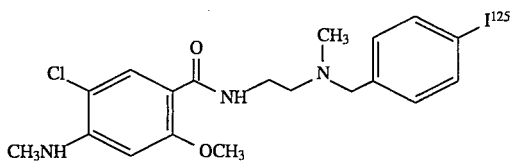

Martres, M. P. et al. *Eur. J. Pharmacol.* 118, 211 (1985), discloses the following compound which is described as a selective ligand for dopamine D2 receptors:

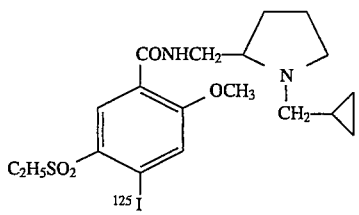

SUMMARY OF THE INVENTION

In accordance with the present invention there is provided a method of radioimaging a human brain comprising the steps of systemically administering a radioiodinated substituted benzamide having high affinity and specificity for dopamine D2 receptors and low to moderate lipophilicity and binding high levels of the substituted benzamide in D2 receptor rich regions and low binding levels in dopamine D2 receptor poor regions. Emitted gamma radiation by the composition is detected and a high contrast image is formed therefrom.

The present invention further provides a radioimaging compound selected from the group consisting of radioiodinated benzamides having a lipophilicity range of about log $k_W$=1.7 to 3.3 at pH 7.5 and a $K_D$ of about 0.15 nM or less.

The advantages of the present invention over those of prior art include the following:

a) Discovery of the structural requirements within the benzamide molecule needed to optimize the combination of lipophilicity and dopamine D2 receptor affinity so as to maximize the image contrast between receptor rich and receptor poor areas;

b) Facile preparation, radioiodination and purification of the compounds identified by a) above;

c) The ability of these radioiodinated benzamides to achieve extremely high imaging contrast and thereby enable improved quantitation of dopamine D2 receptor parameters via SPECT imaging in man. Radiolabelled benzamides of previous art, such as raclopride and IBZM have achieved striatal:cerebellar ratios of 4 and 2 respectively. Radiolabelled spiperone derivatives have achieved ratios of no more than 10 in man. [$^{123}$I]epidepride has produced imaging ratios ranging from 40 to 200 fold greater than previously achieved in man because of the aforementioned ability to optimize lipophilicity and affinity (see FIG. 2); and d) The ability to visualize dopamine D2 receptors in brain regions in man never previously noted either in vivo or in vitro studies, i.e. the thalamus. In vivo studies of dopamine D2 receptors outside of the striatum have not previously been reported in man. These receptors are thought to be involved in the therapeutic actions of neuroleptic drugs and in the pathophysiology of schizophrenia. The present invention, therefore, allows study of biologically important receptors never previously observed or amenable to image analysis in man.

A radiopharmaceutical composition of the present invention comprised of a radioiodinated substituted benzamide and a pharmaceutical carrier such as physiological buffered saline solution. A method for diagnostic imaging comprises the steps of systemically administering to humans an effective amount of radiopharmaceutical composition and subsequently making an image by detecting gamma radiation emitted by said radiopharmaceutical composition following its localization on dopamine D2 receptors in the target organ.

FIGURES AND THE DRAWINGS

The advantages of the present invention will be appreciated by reference to the following detailed descriptions and drawings wherein:

FIG. 1 shows the logarithm of capacity factors at different methanol concentrations for 5-substituted 2,3-dimethoxybenzamides. Both the slope (a) and intercepts (log $k_w$) of the linear regression lines are descriptors of the apparent lipophilicity, log $P_{app}$;

FIG. 2 shows correlation between calculated and measured log $k_w$ using equation 4b for the 6-H and 6-OMe (orthopramide) series and equation 5 for the 6-OH (methoxysalicylamide) series;

FIG. 3 shows antidopamine activity (-log $K_i$ for blocking [$^3$H]spiperone binding) of N-alkyl and N-(ω-fluoroalkyl) derivatives of raclopride plotted against their apparent lipophilicity at pH 7.5 (log $P_{app}$). The decrease in activity caused by the introduction of an aliphatic fluorine atom seems to be the consequence of the increase in log $P_{app}$, in particular with 2-fluoroethyl substitution;

Figure 9:
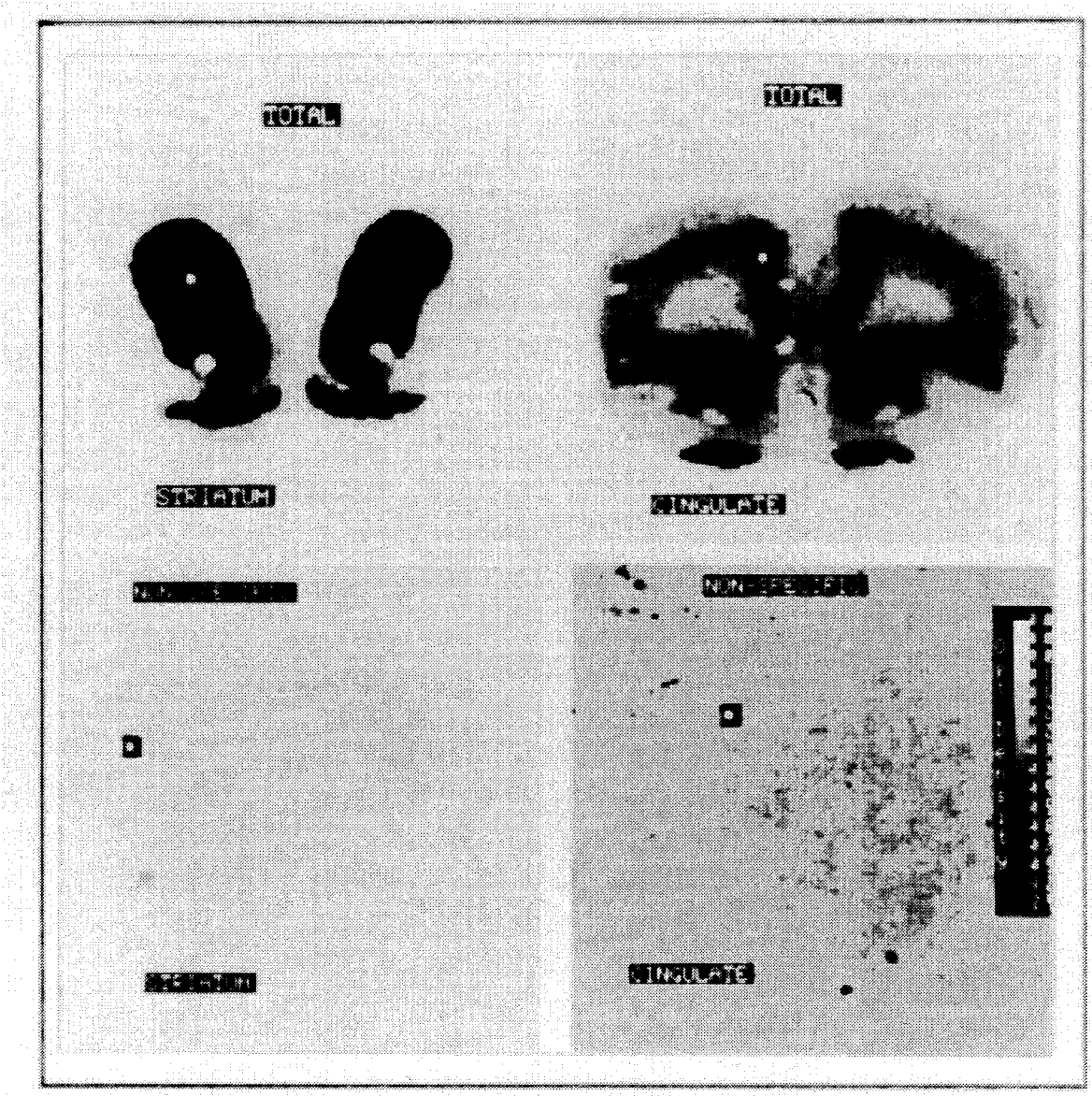
Figure 8:
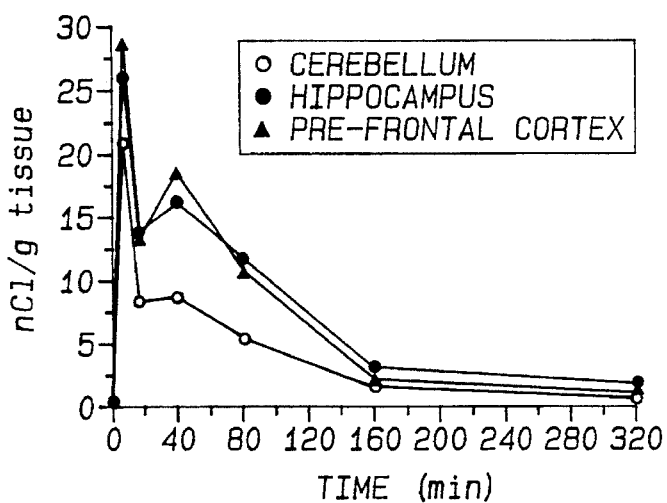
Figure 10A:
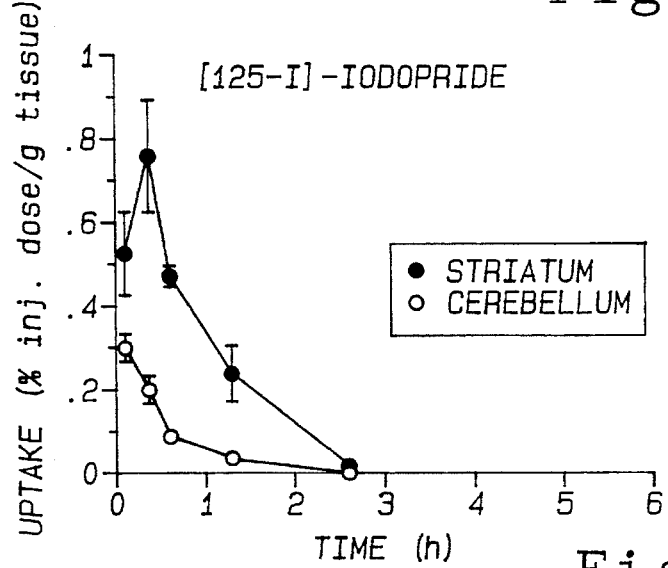
Figure 10B:
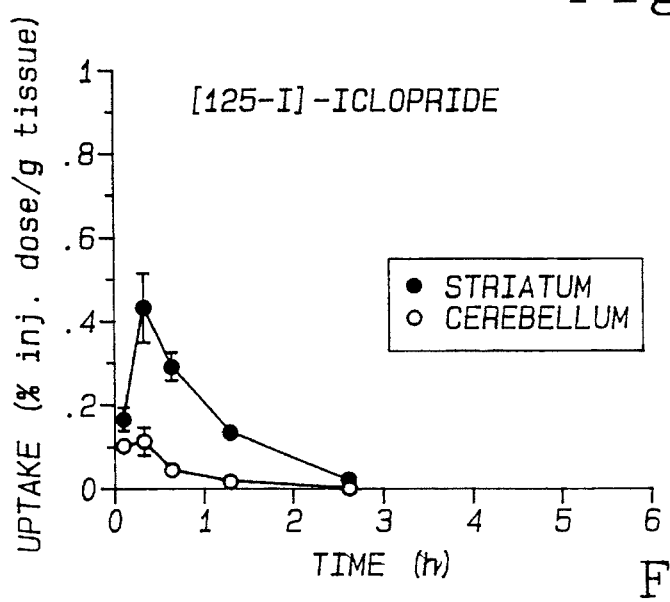
Figure 10C:
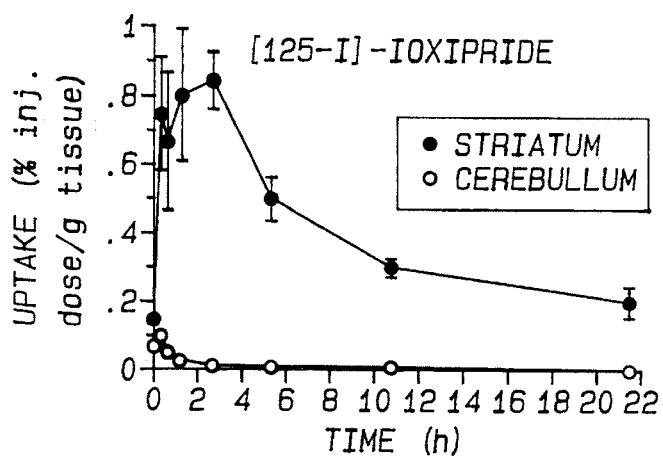
Figure 10D:
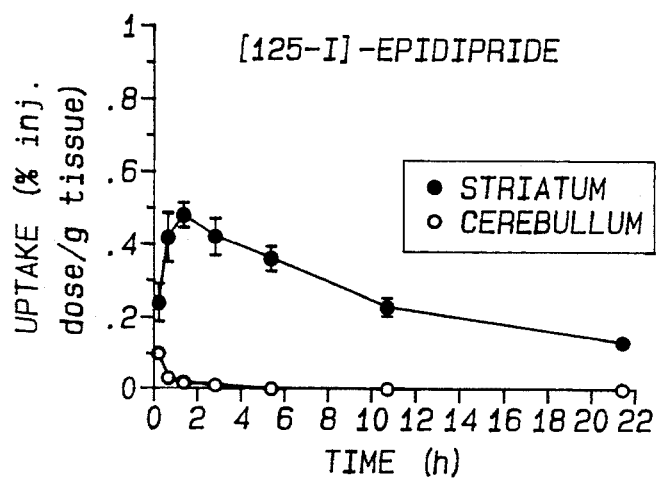
Figure 11A:
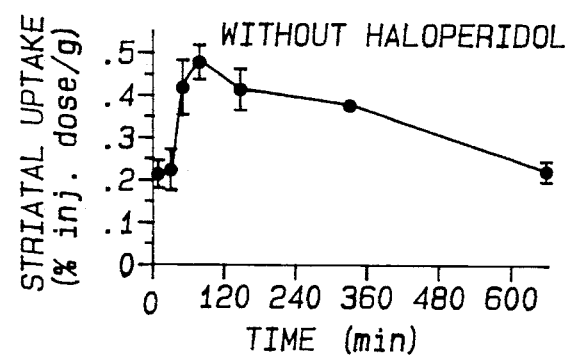
Figure 11B:
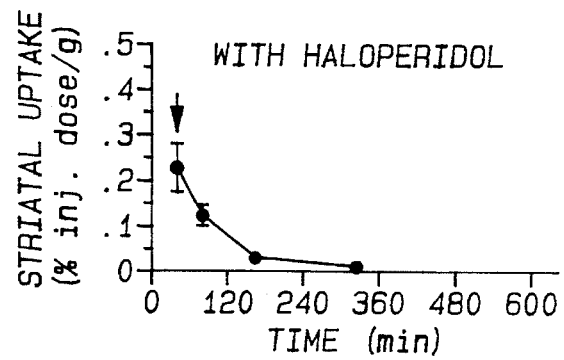
Figure 12A:
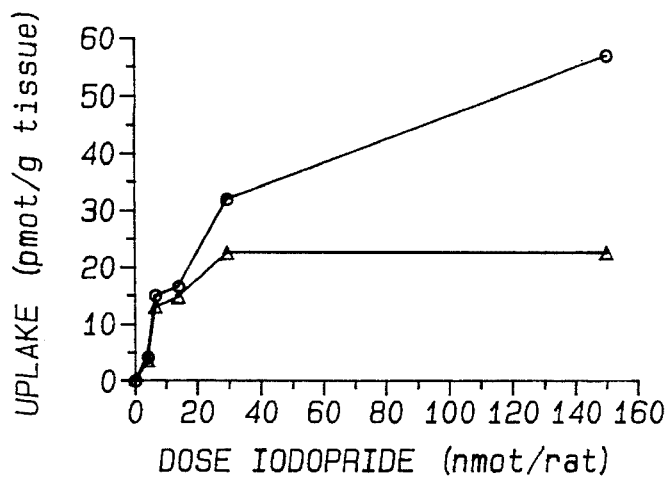
Figure 13:
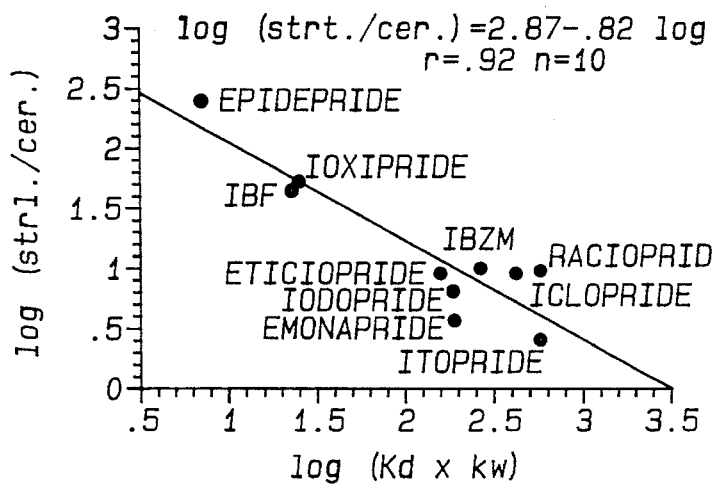
Figure 14:
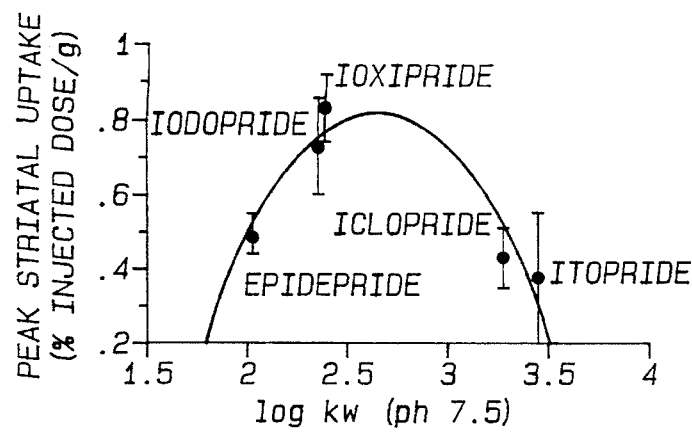
Figure 15:
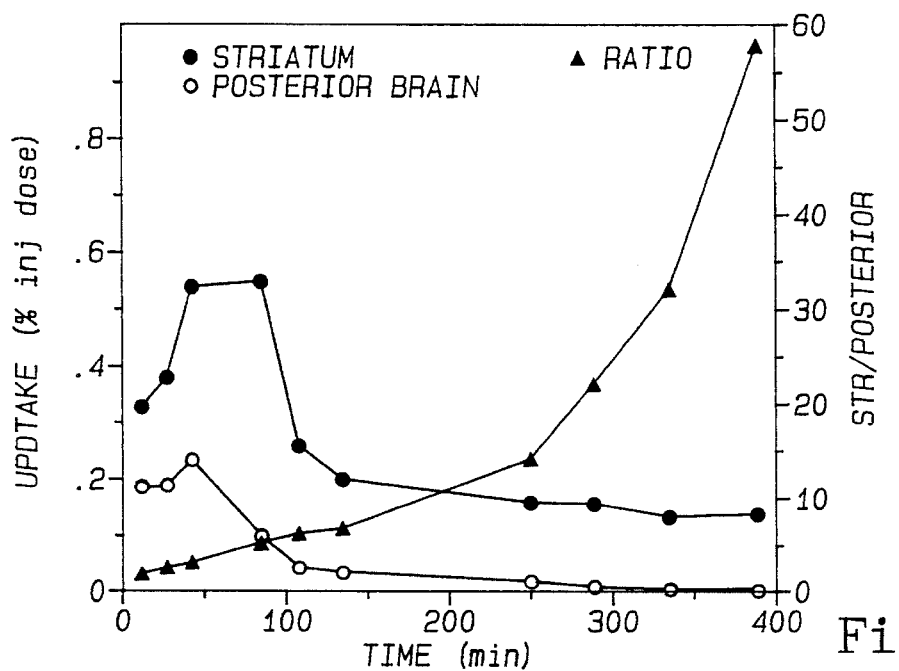
Figure 16:
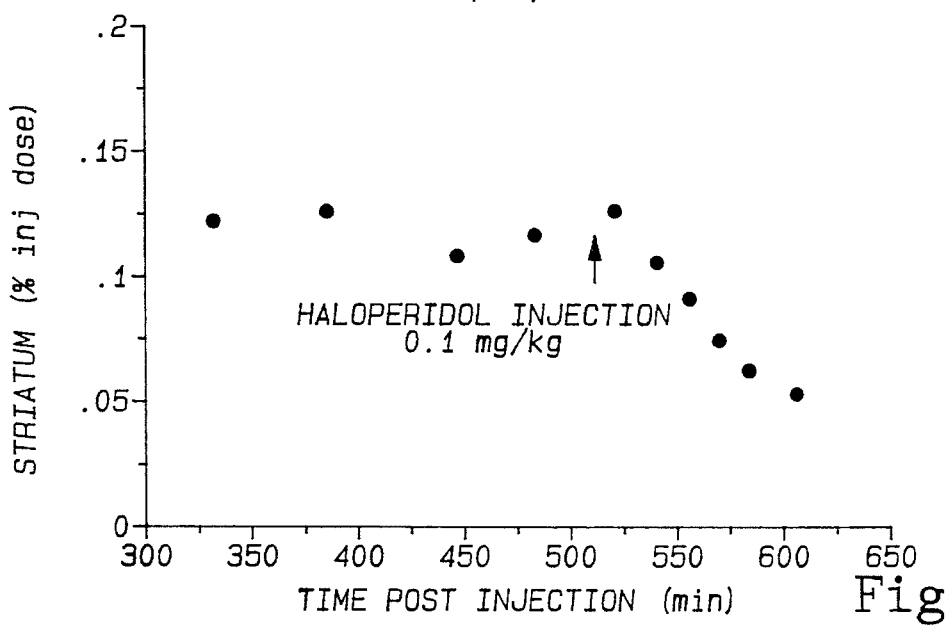
Figure 17:
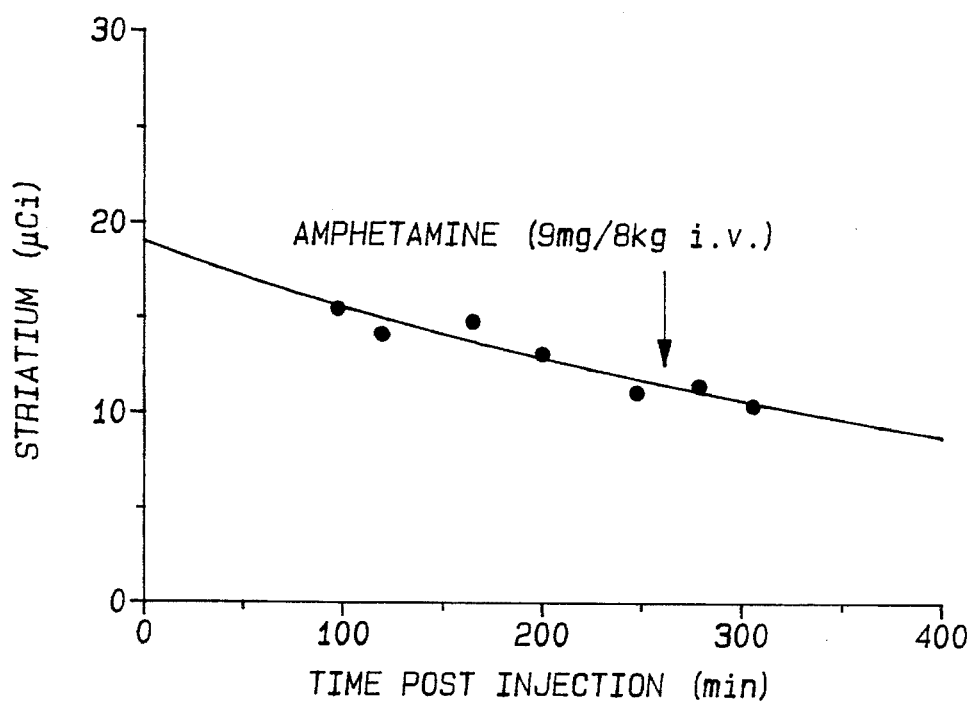

FIG. 7 shows a Scatchard analysis of [$^{125}$I] epidepride binding to A. striatal; B. medial frontal cortical; C. hippocampal; and D. cerebellar homogenates. KD's (pM) and Bmax's were A. 24.4 pM and 36.7 pmol/g striatum, B. 24.0 pM and 1.04 pmol/g medial frontal cortex, C. 24.1 and 0.85 pmol/g hippocampus and 24.4 pM and 0.37 pmol/g cerebellum;

FIG. 8 shows an in vivo uptake in rat medial frontal cortex, hippocampus and cerebellum from 5 to 320 min following intravenous injection of 25 μCi [$^{125}$I]epidepride. The ratios of medial frontal cortical and hippocampal:cerebellar uptake were both 2.2:1 at 80 min post injection;

FIG. 9 shows in vitro autoradiograms of [$^{125}$I]epidepride binding to coronal sections through striatum and prefrontal cortex. Dense labelling is seen in striatum and layers V and VI of prefrontal and supragenual cingulate cortices. (+)-Butaclamol (1 μM) reduced binding to background levels in all structures;

FIG. 10 shows a time course of in vivo rat brain uptake of [$^{125}$I] radioiodinated benzamides in rat striatum and cerebellum. Each point is the mean of four animals±s.d. Rats were injected in the tail vein at t=0 and killed at the indicated time points;

FIG. 11 shows in vivo displacement of [$^{125}$I]epidepride by haloperidol. (A) Time course of [ $^{125}$I ] epidepride without haloperidol. Each point is the means of four animals±s.d. (B) Haloperidol displacement. Forty minutes after [$^{125}$I]epidepride injection, haloperidol (5 mg/kg, i.v.) was administered and groups of animals killed at times up to 320 min. A monoexponential washout (t½=40 min) was seen;

FIG. 12 shows in vivo saturation of the dopamine D2 receptor in rat brain. (A) [$^{125}$I]iodopride saturation. Groups of four rats were injected intravenously with 30 μCi [$^{125}$I] iodopride with specific activities ranging 20 to 0.2 Ci/mmol. Rats were killed at 60 minutes after injection. No saturation was demonstrated using cerebellum as a measure of non-specific binding and free ligand; saturation was shown when frontal cortex was used to estimate nonspecific binding plus free ligand. (B) [$^{125}$I]epidepride saturation. Groups of four rats were intravenously administered 25 μCi [$^{125}$I]epidepride with specific activities ranging from 100 to 0.2 ci/mmol and killed at 80 minutes after injection. Cerebellar uptake was used as a measure of nonspecific binding plus free ligand;

FIG. 13 shows correlation of peak striatal:cerebellar ratios in rat brain with the product of the dissociation constant ($K_D$) and the apparent lipophilicity ($K_W$, pH 7.5). The dissociation constants, log $K_W$'s and striatal:cerebellar ratios are taken from Table 1 and the literature; and FIG. 14 shows a relationship between apparent lipophilicity (log $k_W$) at pH 7.5 and peak striatal uptake (% administered dose/gram tissue in the rat brain). Peak uptake occurred between log $k_W$ of 2.4 to 2.8. Each point is the means of four animals±s.d.;

FIG. 15 shows plots of striatal radioactivity, posterium brain radioactivity, and striatal: posterior brain ratios;

FIG. 16 shows the effect of haloperidol on [$^{123}$I]epidepride binding;

FIG. 17 shows the effect of amphetamine on the same system as FIG. 16; and

Figure 18:
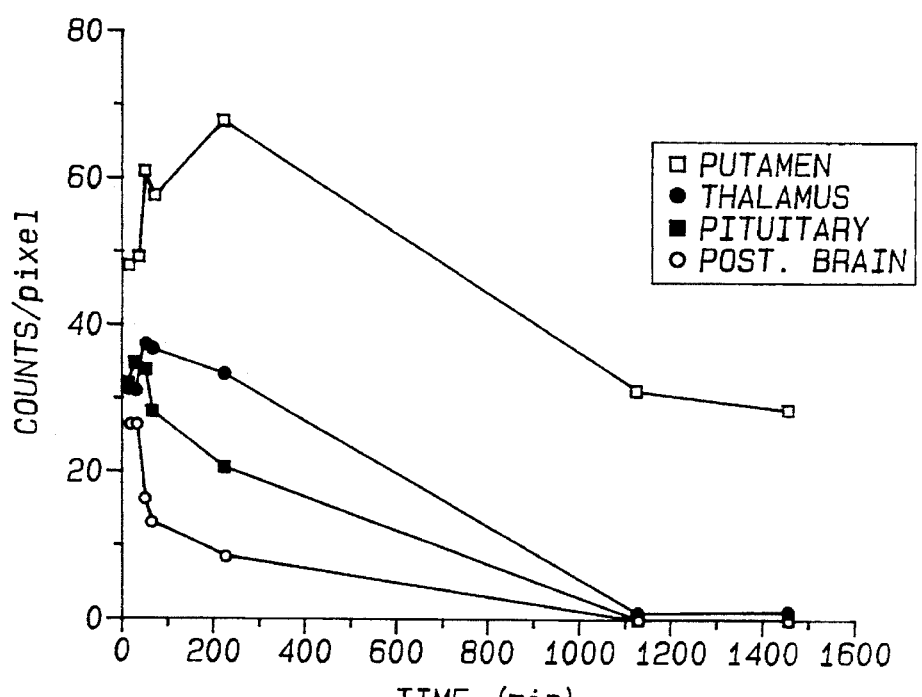

FIG. 18 shows time activity curves of regional brain uptake of [$^{123}$I]epidepride in man.

DETAILED DESCRIPTION OF THE INVENTION

The present invention provides a method of radioimaging dopamine D2 receptors in human brain by systemically administering a radioiodinated substituted benzamide. The benzamide is selected for having an optimal combination of high affinity and selectivity for dopamine D2 receptors and low to moderate lipophilicity. This selection is made possible by the discovery reported herein, of the factors needed to accomplish this optimization. Use of a compound that meets the discovery criteria results in high levels of uptake in D2 receptor rich regions and low levels of uptake in D2 receptor poor regions.

Radiation emitted by the composition is detected and an image with high contrast is therefrom. As a result of the above, epidepride, ioxipride, and their 2-ethoxy homologs discussed in detail hereafter, are superior single photon emission tomography ligands for the study of the dopamine D2 receptor. Specifically, it has been discovered that for optimal brain uptake and high image contrast, a moderate to low lipophilicity, corresponding to a log $k_W$ of 1.7 to 3.3 and a $K_D$ of 0.150 nM or less, are required for imaging in accordance with the present invention. These compounds are prepared at high specific activity (greater than 2000 Ci.mmol) with $^{125}$I, or at higher specific activities when labelled with $^{123}$I.

The combination of the above properties has allowed Scatchard analysis of in vitro binding to dopamine D2 receptors not only in regions with low dopamine D2 receptor density, such as the cortex, hippocampus, but also in the cerebellum, an area with extremely low dopamine D2 receptor density. Further, it was found that $^{123}$I-labelled compounds, made in accordance with the present invention, are superior ligands for single photon tomographic imaging of dopamine D2 receptor in man, providing 40 to 200 fold higher contrast than previously reported and the ability selectively label extrastriatal dopamine D2 receptors in thalamus, cortex, hypothalamus and pituitary. Human extrastriatal dopamine D2 receptors cannot be visualized by SPECT imaging with radioligands of the prior art.

Substituted benzamides which have been chosen based on the selection criteria of optimal lipophilicity in addition to high affinity and selectivity for the dopamine D2 receptor and undergo the radioiodination reaction of the present invention are either known compounds or can be formulated by the following procedures. These benzamides can be obtained by reacting either a bromine or iodine substituted benzamide with a bis(trialkyltin) reagent in the presence of a palladium catalyst. For example, substituted benzamide derivatives are represented by the formula:

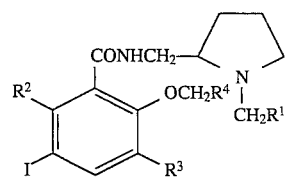

wherein $R^1$ is a hydrogen atom, a lower alkyl group consisting of 1–4 carbon atoms, a cycloalkyl group consisting of 3–6 carbon atoms, an alkenyl group which contains 2–4 carbon atoms, or an alkenyl group consisting of 2–4 carbon atoms; $R^2$ is a hydrogen atom or a hydroxyl group; $R^3$ is a hydrogen atom (unless $R^2$ is a hydroxyl group), a chlorine atom, a methoxy group, or a methyl group, and $R^4$ is a hydrogen atom or a methyl group. These may be obtained by the reaction of the intermediate compound II:

[Structure: benzamide with CONHCH₂-(pyrrolidine N-CH₂R¹), OCH₂R⁴, R², (R⁵)₃Sn, R³ substituents]

wherein R⁵ is an alkyl group and R¹–R⁴ are defined as for compound I, with a radioactive isotope of iodine in a protic solvent such as ethanol or hydrochloric acid. The iodine can be generated in situ by decomposition of iodine monochloride or by oxidation of the alkali metal iodide with hydrogen peroxide or an agent such as the sodium salt of N-chloro-p-toluenesulfonamide.

The benzamide compounds of this invention can be obtained by acid-catalyzed iododestannylation of the corresponding trialkyltin derivatives. The radioiodination technique is illustrated in the examples. $^{125}$I radioligands are preferably employed as in vitro while $^{123}$I- and $^{131}$I-radioligands are employed as in vivo imaging agents for the brain.

A pharmaceutical composition of the present invention comprises one of the aforementioned isotopes of radioiodinated substituted benzamides and a carrier such as physiological buffered saline solution. It is contemplated that the composition will be systemically administered to the patient as by intravenous injection. Suitable doses for use as a diagnostic imaging agent are from about 2 to about 20 mCi of $^{123}$I-labelled iodobenzamides for D2 dopamine receptors; that is, as imaging agents for the brain.

It will be appreciated by those skilled in the art that the novel imaging agents of the present invention are employed in accordance with conventional methodology in nuclear medicine in a manner analogous to functional brain imaging. Thus, a composition of the present invention is systemically administered to the patient and subsequently the uptake of the composition in the selected organ is measured and an image formed, for example, by means of a conventional gamma auger CT camera.

Further understanding and use of the present invention can be obtained from the examples and from Budinger, T. F. Physical Attributes of Single-Photon Tomography, *J. Nucl. Med.* 21:579–592 (1980).

In the process of preparing the radiolabelled substituted benzamides of the present invention, the radioactive iodine atom is introduced in the last step of the synthesis. In this manner, the radiation hazard will be limited in the preparation and purification of the ligands.

The compounds of the present invention are characterized as having high affinity and selectivity for dopamine D2 binding sites in addition to low to moderate lipophilicity. More specifically, they can be represented by the Formula III:

[Structure: benzamide with CONHCH₂-pyrrolidine(N-CH₂R¹), OCH₂R⁴, R², R⁵, R³]

wherein R⁵ is $^{123}$I, $^{125}$I, or $^{131}$I, and R¹–R⁴ are as defined above for compound I.

Preferred compounds of the present invention are:

Formula IV
[Structure with $^{123}$I, OCH₃, OCH₃, CONHCH₂-pyrrolidine-N-C₂H₅]

Formula V
[Structure with $^{123}$I, O-C₂H₅, O-CH₃, CONHCH-pyrrolidine-N-C₂H₅]

Formula VI
[Structure with HO, $^{123}$I, OCH₃, OCH₃, CONHCH₂-pyrrolidine-N-C₂H₅]

The above-noted compounds are used to detect, visualize and analyze the distribution of the dopamine D2 receptor in the mammalian brain as their optically resolved enantiomers.

Suitable iodine isotopes for single photon emission tomography or autoradiography are iodine-123 for maximum specific radioactivity at $9 \times 10^6$ Ci/mmol, iodine-125 for $2 \times 10^3$ Ci/mmol, and iodine-131 for $1.6 \times 10^4$ Ci/mmol.

Compounds of the present invention can be obtained by one of the following methods of synthesis.

Compound A
[Structure: benzamide with CONHCH₂-pyrrolidine(N-CH₂R¹), OCH₂R⁴, R², (R⁵)₃Sn, R³]

Compounds of formula A, wherein R⁵ is an alkyl group of 1 to 5 carbon atoms such as n-butyl, R¹, R², R³ and R⁴ are defined as before, are treated with radioactive iodine in a protic solvent such as ethanol or dilute hydrochloric acid. The iodine can be generated in situ by oxidation of sodium iodide with hydrogen peroxide or chloramine-T (sodium salt of N-chloro-p-toluenesulfonamide), or by using radioactive iodine monochloride.

Alternatively, the compounds of the present invention may be synthesized by the following method.

Compound B
[Structure: benzamide with CONHCH₂-pyrrolidine(N-CH₂R¹), OCH₂R⁴, R², R³]

Compounds of formula B, wherein R², R³ and R⁴ are defined as in Formula I, are treated with radioactive iodine in a solvent such as chloroform or dioxane at elevated temperature.

Experimental Examples

The examples presented hereafter provide documentation of the studies which underline the current invention. These examples consist of: 1) data concerning the structure activity and lipophilicity relationships for a series of substituted benzamides leading to the discovery, reported herein, of the structural criteria required to produce radioiodinated benzamide structures that possess superior properties for in vivo and in vitro studies of dopamine D2 receptors; 2) methods and procedures fir synthesis and/or radioiodination of the benzamides structures identified by the above discovery; 3) studies regarding the use of the radioiodinated benzamides of choice for receptor binding studies, autoradiography of dopamine D2 receptors in brain; 4) studies which demonstrate the relationship between log $k_W$, $K_D$ and in vivo rat striatal uptake for selected radioiodinated benzamides, as well as ex vivo regional brain uptake studies; 5) studies regarding the use of radioiodinated benzamides of choice for SPECT imaging of dopamine D2 receptors in monkey brain; and 6) studies regarding the use of radioiodinated benzamides of choice for SPECT imaging for dopamine D2 receptors and for in vitro binding studies in human brain. Collectively, these examples delineate the factors leading to the discovery of the invention regarding the selection of superior radioiodinated benzamide ligands, outline the development of facile methods for their synthesis, purification and preparation for systemic administration to primate and human subjects, and demonstrate the superiority of the radioiodinated ligands so chosen over ligands of the prior art for the study of striatal and especially extra-striatal dopamine D2 receptors in brain.

EXAMPLE 1

Methods

Lipophilicity by HPLC—The Biagi method as described by El Tayar[36] was utilized for estimating the lipophilicity of substituted benzamides. The compounds were analyzed by C-18 reverse phase chromatography using a 3-N-(morpholino)propanesulfonic acid (MOPS) buffer (20 mM, pH 7.50) containing 2.0 ml per liter of n-decylamine and methanol concentrations between 25% and 65%. The capacity factor ($k_x$) at various methanol concentrations was calculated using equation 1a.

$$k_x = (t_x - t_o)/t_o \quad (1a)$$

$$\log k_x = a\,x + b \quad (1b)$$

where $t_x$ is the retention time of the compound and $t_o$ is the retention time of the void volume (methanol). The logarithms of the capacity factors (log $k_x$) were plotted against methanol concentration and the log $k_W$ was obtained by linear extrapolation to 0% methanol concentration according to equation 1b. The intercept value (b) represents the apparent lipophilicity at pH 7.50. Multiple log $k_W$ determinations at different times and with different batches of HPLC columns and buffers were averaged. The HPLC system consisted of a Kontron 420 pump, a Rheodyne 4125 injection valve, a 25 cm×4.6 mm Lichrosorb RP-18 10 μm HPLC column (Alltech) protected by a waters Resolve C-18 Guard-Pak column, and a kontron 430 scanning UV detector operating at 235 nm. The column was operated at ambient temperature (21° C.) and a flow rate of 1.5 ml/min. Once a week, the column was back-flushed with 100% methanol in the attempt to maintain the original partitioning conditions. However, while the capacity factors obtained with new columns were reproducible, the retention times showed a progressive increase over several weeks of use. In order to compare data recorded at different times, the retention times of all compounds were normalized to match the capacity factors of epidepride (e.g. $k_{50}$ 5.19) or raclopride (e.g. $k_{50}$ 9.28) for each concentration of methanol. The columns were replace when this correction factor exceeded 10%.

Partitioning by Shake-Flask Method— Standard solutions (10 mM) of the compounds in 50% aqueous ethanol (0.05 ml) were added to a of 5.0 ml 1-n-octanol and 5.0 ml 3-N-(morpholino)-propanesulfonic acid (MOPS) or disodium phosphate buffer (20 mM, pH 7.5, 21° C.). The mixture was shaken for 5 min. A sample of the aqueous layer (0.100 ml) was analyzed on the RP-18 column (Alltech) and the amount before ($n_o$) and after shaking ($n_{aq}$) was determined by comparison of its UV absorption at 235 nm (peak area) with that of 2–100 nmol of the stock solution. The log $P_{oct}$ values were not corrected for partial molar volumes of water in octanol (3.8%) and octanol in water (0.11%)[37] nor corrected for the partial ionization of the benzamide molecule.

Amine and Phenol Ionization— ionization constants of the tertiary amine of the N-[2-(aminomethyl)pyrrolidinyl] group were taken from the work of Van Damme et al.[37] They determined the $pK_a$ for a series of 3- and 5-substituted N-(2,2-diethylaminoethyl)benzamides. Correlation of the reported values with the sum of the Hammett σ constant gave a reaction constant of −0.28 (±0.10)$\Sigma\sigma_{3,5}$meta. By adding the substituent values for the 2-methoxy and 6-hydroxy groups and correcting to fit the two known $pK_a$(NH) for iodopride (8.89) and raclopride (9.21), the following relationship was obtained (Equation 2a).

$$pK_a\,(NH) = 9.08 - 0.28\Sigma\sigma_{3,5}m - 0.72\Sigma\sigma_{4,6}p \quad (2a)$$

The ionization constants of polysubstituted phenols, $pK_a$(OH), can be obtained by calculating the effects of each substituent according to Biggs and Robinson.[38] Their reported values give reaction constants ρ of 2.3 and 3.8 for the ortho and para positions, respectively. Titration values of a series of alkyl and halogen substituted 6-methoxysalicylamides (A. Ohlberger, unpublished) give a similar relationship (Equation 2b).

$$pKa(OH) = 8.06 - 3.79\Sigma\sigma_{3,5}p + 2,4m \quad (2b)$$

At pH 7.5, correction of the lipophilicity for both the protonation of the amine and the discussion of the acidic phenol is given by Equation 2c. When $pK_a$(OH)<$pK_a$(NH), the molecule forms a zwitter ion in which these pseudo ionization constants are not exactly identical to the true constants.[1] However, his difference is small compared to the total value of the correction factor, and was ignored.

$$\log k_W^\circ = \log k_W(pH) + \log[1 + 10^{pKa(NH)-pH} + 10^{(pH-pKa(OH)}] \quad (2c)$$

Regression Analysis—Calculation of capacity factors and linear regression of the log $k_x$ values were performed with standard statistical software. Multiple regression analysis of the log $k_W^\circ$ values and Hansch aromatic lipophilicity constants (π)[39], Hammett aromatic electronic constants (σ)[39,40], and Fujita susceptibility constants (ρ)[40] to account for cross-interactions, were performed using Microsoft Statwork software. Regression coefficients are given with their 95% confidens intervals. The cross-interaction term ($T_{ij}$) between the ith and the jth aromatic positions were calculated as the sum of the mutual electronegativity (σ) and susceptibility (ρ) according to equation 2a.[40] The calculated log $k_W$ was obtained by multiple regression fit using equation 2b. When appropriate, substituent parameters for certain positions such as ortho to the common methoxy or carboxamido substituents were replaced by indicator values ($R_3$, $R_6$).

$$T_{ij} = \rho_i \sigma_j + \rho_j \sigma_i \quad (3a)$$

$$\log k_W = a \Sigma \pi_i + b \Sigma T_{ij} + c \quad (3b)$$

RESULTS

Apparent Lipophilicities

Octanol-buffer partitioning of representative compounds are shown in Table 1. Comparison of the log $P_{app}$ for these selected compounds with log $k_W$ showed the following relationship.

$$\log P_{app} = 1.174 \log k_W - 0.688 \quad (4)$$

$$r = 0.96 \quad n = 14 \quad s = 0.39 \quad F = 24.6$$

6-H Series

The linearly extrapolated intercept of log $k_x$ at zero % methanol (log $k_w$) for the substituted benzamides are shown in Tables 2a and 2b. The slope of the regression line can also be correlated with lipophilicity.[42] The slope of the line, the number of methanol concentrations, and the correlation coefficient are also given in Tables 2a and 2b. The intercept represents the apparent lipophilicity at pH 7.5. Because the regression for all these compounds was highly linear with correlation coefficients r>0.99, we have also included results with some compounds for which only two methanol concentration were used.

Figure 1:
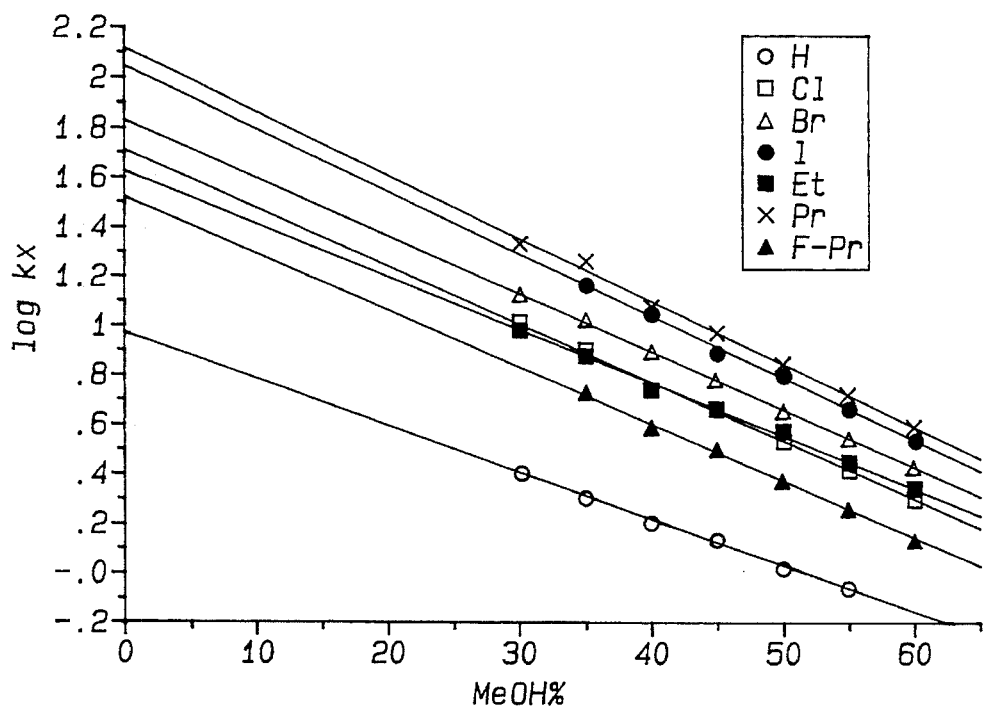

Changes in log $k_W$ with different aromatic substituents in the 2-methoxybenzamide series (Table 2a) followed the Hansch π values with two exceptions. While the contribution of halogen atoms in the aromatic 5-position to the apparent lipophilicity was close to their Hansch π values (99%), ethyl and n-propyl groups contributed only about 70% of their corresponding π value. This is illustrated in FIG. 1 which shows the slopes and intercepts of some compounds in the 3-OMe, 6-H (epidepride) series. The other exception was the fact that throughout this series, an additional methoxy substituent in the aromatic 3-position caused an average decrease in log $k_W$ of 0.22. The effect of homologization of the 2-methoxy group increased the apparent lipophilicity by 0.25 log $k_W$ units while the same substitution in the 3-position caused a 0.42 unit increase (Table 2b).

Increased chain length of the 2- and 3-alkoxy derivatives resulted in increases in lipophilicity, as expected. Correlation of log $k_W$ with the sum of w-values and the sum of ortho, meta, and para cross-interactions[40] gave the following equation.

$$\log k_W° = 2.54\ (\pm 0.06) + 0.72\ (\pm 0.07) \Sigma \pi_{2,3,5} + 0.89\ (\pm 0.16) \Sigma \rho \sigma(o,m,p) \quad (4a)$$

$$r = 0.96 \quad n = 26 \quad s = 0.14 \quad F = 91$$

Improved statistics was obtained when the aromatic 3-substituent was denoted by an indicator value. This method allowed the 2,6-dimethoxy series ($R_6$) to also be included. Separating the type of cross-interactions in Equation 4a showed that the meta interaction, i.e. $T_{13}+T_{15}T_{35}$, explains 80% of the variation (Equation 4b).

$$\log k_W°(6\text{-H,OMe}) = 2.60(\pm 0.04) + 0.079(\pm 0.04)\Sigma \pi_{2,3,5,6} + \quad (4a)$$

$$0.79(\pm 0.10)\Sigma \rho \sigma(m) - 0.21(\pm 0.04)\ R_3 - 0.60(\pm 0.04)R_6$$

$$r = 0.98 \quad n = 31 \quad s = 0.10 \quad F = 201$$

r=0.98 n=31 s=0.10 F=201

6-OH (Methoxysalicylamide) Series (Table 3)

The linearly extrapolated intercept of log $k_x$ at zero % methanol (log $k_W$) for the substituted 6-methoxybenzamides are shown in Table 3 (for clarity, the numbering order of the 2-methoxybenzamides were used). Increase in log $k_W$ resulting from the 6-hydroxy group averaged 0.56 units. Close examination revealed that for 5-halogen substituted benzamides the increase was 0.42, while for the 5-alkyl series the increase was 0.80 units (Table 3). Contribution of halogen atoms in the aromatic 5-position to the apparent lipophilicity was close to their nominal π values. In contrast to the results of the 6-H series, ethyl and n-propyl groups in this position contributed about 120% of their π values. In the aromatic 3-position (5-position of the 6-methoxysalicylamides), however, only about 50% of the contribution of either halogen or alkyl substitution were manifested in the global apparent lipophilicity. Correlation of log $k_W$ by addition of the aromatic substituent values including the product of susceptibility and electronegativity according to the method of Fujita[40] gave large errors in the calculated values. However, attempted multiple correlations with the different cross-interaction terms produced a useful equation (Equation 5).

$$\log k_W°(6\text{-OH}) = 3.96(\pm 0.04) + 1.15(\pm 0.04)\Sigma \pi_{2,3,5,6} + \quad (5)$$

$$2.00(\pm 0.68)T_{1,3} + 13.8(\pm 1.7)T_{2,5} -$$

$$4.7(\pm 0.66)T_{5,6} - 0.65(\pm 0.11)R_3$$

$$r = 0.99 \quad n = 25 \quad s = 0.11 \quad F = 179$$

r=0.99 n=25 s=0.11 F=179

The cross-interaction term (T) was calculated according to equation 2a. Any other combination of substituent parameters gave lower Fisher ratios (F) and/or higher standard errors (s). The coefficient for the indicator of the presence of a substituent in the 3-position ($R_3$) is twice that seen in equation 4b, suggesting that the susceptibility for stearic perturbation of the amide hydrogen bond is increased in the salicylamide series. Of the combined cross-interaction terms, only one of each ortho-, meta-, and para-interaction displayed a meaningful correlation with the observed apparent lipophilicities.

Effects of Fluorine (Tables 2–4)

Compounds with 5-fluoroalkyl substituents in the aromatic ring were considerably less lipophilic than the corresponding alkyl derivatives. The decreasing effect of an aliphatic fluorine atom was about 0.6 in good agreement with that reported by Brandstrom.[38] Substitution with a 2-fluoroethyl group in the 2-alkoxy position decreased the apparent lipophilicity by 0.22 units compared to the corresponding desfluoro analogues, thereby making the lipophilicity of the 2-fluoroethoxy group equivalent to that of a methoxy group. effects were also seen in the aromatic 3-position (compound 31 versus 30).

Increases in chain length of the substituent on the tertiary amine nitrogen atom of the pyrrolidine ring increased the apparent lipophilicity by 0.3 units per carbon atom (Table 4a). Introduction of fluorine in the alkyl chain caused a drastic increase in log $k_W$ by 1.3 compared to the corresponding N-ethyl compound in the 2,3-dimethoxybenzamide (epidepride) series (Table 4a) and by 1.5 in the 6-methoxy-salicylamide (raclopride) series (Table 4b). At a distance of 3 carbon atoms, the increase was 0.5 units. Thus, the effect of fluorine substitution in the N-alkyl group on log $k_W$ was opposite that found in the 5-alkyl and 3-alkoxy series. Since the lipophilicity in the desfluoro series increased with chain length about 0.3–0.4 units, the effect of fluorine was found to follow a linear function of the logarithm of the number of carbon atoms (n) between the fluorine and amine nitrogen atom (Equation 5).

$$\log P_{app}(N\text{-alkyl-}F) = \log P_{app}(N\text{-}Et) + 0.35(n-2) - 4.1 \log n + 2.48 \quad (5)$$

Conformational Effects (Table 5)

The apparent lipophilicities of 2,6-dimethoxybenzamides are shown in Table 5. The presence of two ortho substituents in these benzamides reduced the log $k_W$ by 0.6 units. In contrast to the results of the previous series, an additional 3-methoxy group caused a further decrease of only 0.1 units, supporting the view that conformational effects on the benzamide moiety play a major role in explaining the influence of the 3-substituent.

The results of iodine substituted benzamides with potential use as SPECT imaging agents including that of IBF are summarized in Table 6a. Their relative apparent lipophilicity in comparison to that of epidepride demonstrates that epidepride is the receptor ligand that have the lowest log P of all agents, a fact that has been attributed to causing the exceptionally high regional contrast seen with radiolabelled epidepride (see discussion). Table 6b shows the summary of corresponding fluorine substituted potential PET agents, including MPB and MABN,[35] and their relative apparent lipophilicity in comparison to that of FPMB.[15] Only the corresponding des-3-methoxy-2-fluoroethyl analogue (7) had a lower log P value (0.80) in excellent agreement with the reported log $P_{oct}$ of 0.81 for this compound[14]

DISCUSSION OF EXAMPLE I

The objective of this study was to measure log $P_{app}$ of a series of structurally related substituted benzamides and thereby determine the aromatic substituent effects on the apparent lipophilicity at pH 7.5. In particular, a basis was established for quantitative understanding of the effects of iodine and fluorine substitution in various positions in the aromatic nucleus to aid in the design of optimal substituted benzamides for use as non-invasive SPECT imaging agents of cerebral dopamine D2 receptors in man.

Lipophilicity can be factorized into separate terms representing stearic (bulk) properties and electronic (polar) properties. The bulk term can be described by such parameters as molar volume or the Hansch π value. The polar term is usually more difficult to parameterize and it is considered as expression of the dipole-dipole polarizability in the molecule and hydrogen bond formation. Herein, the polar term is expressed using the Hammett σ parameter by the method of Fujita[40] and applied by Tsantili-Kakoulidou et al.[43]

Substituted 2-methoxybenzamides (orthopramides) have a planar conformation due to the hydrogen bond between the amide hydrogen atom and the oxygen atom of the methoxy group. The introduction of a hydroxy group in the aromatic 6-position would not be expected to change the amide conformation since coplanarity with the benzene ring is already accomplished by the amide to methoxy hydrogen bond.[11] The hydroxy group increased the log $k_W$ ny 0.4–0.8 compared to the corresponding deshydroxy compound. Introduction of a 6-methoxy group forces the amide moiety out of plane with respect to the aromatic ring due to stearic interaction with the carbonyl group. This should cause a decrease to the apparent lipophilicity and, indeed, an average decrease in log $k_W$ of 0.8 in comparison of the corresponding 6-hydroxy derivative was observed (Table 5). In the methoxysalicylamide series, the acidity of the phenolic hydrogen atom causes the pyrrolidine ring to adopt a unique conformation in relation to the benzamide moiety as a result of the formation of an intramolecular zwitterion. The observed substituent effects on the apparent lipophilicity probably reflect changed in the ionic strength of this inner salt.

Figure 2:
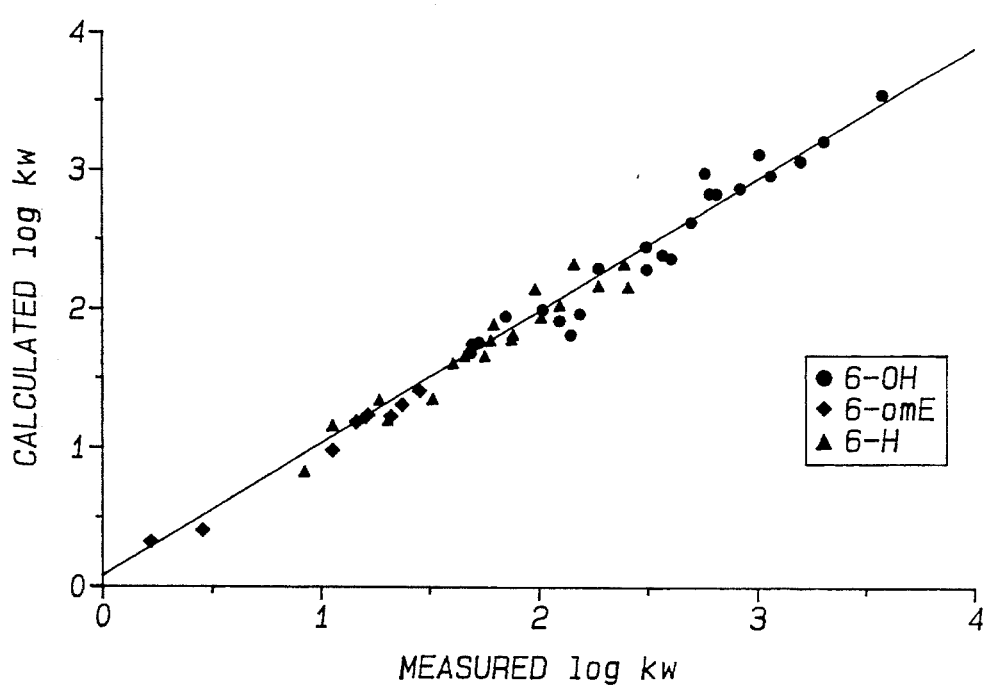

Principal component analysis of the $^{13}C$-NMR chemical shifts of the aromatic carbon atoms have clearly demonstrated that substituted benzamides with a 6-hydroxy group (methoxysalicylamides) are markedly different from those that either lack substituent or have a methoxy group in this position. The excellent correlation between experimentally determined and calculated log $k_W$ using different equations is shown in FIG. 2. Attempts to combine the substituent effects on lipophilicity for the 6-H and 6-OH series gave poor statistics with large correction factors for cross-interaction (not shown). The increase in apparent lipophilicity induced by the 6-OH group, i.e. 0.4 for the 5-halogen series and 0.8 for the 5-alkyl series, is possibly due to a masking effect on polarity of the maide, and therefore making it less susceptible to intermolecular interactions. This effect would depend directly on the strength of the phenol as a weak acid and consequently would be influenced by the electronic properties of the aromatic substituents. The 6-methoxysalicylamides having the most acid phenol, i.e. 3,5-dihalogen compounds such as raclopride (40) with $pK_a$ 5,8[44] actually displayed the smallest increase in log $k_W$ while the largest increase was seen with compounds having an alkyl group adjacent to the hydroxy group, such as eticlopride (43). Therefore, other factors must be involved in the generation of the unexpected high lipophilicity of the 3(5)-alkyl derivatives in the raclopride series. A more plausible explanation for this increase is that the 6-OH group exerts a strong cross-interaction effect with its adjacent 5-substituent, causing the electron-donating alkyl substituent to have the opposite effect than the electron-withdrawing halogen atoms.

Halogen atoms such as bromine and iodine were similar in their contribution to the apparent lipophilicity with iodine being the most lipophilic atom, as expected. This is probably reflected in the close similarity in pharmacological properties between iodine and bromine substituted benzamides. For example, isoremoxipride (11) with log P 1.72 has one of the highest reported potencies ($ED_{50}$ 0.002 µmol/kg i.p.) for antagonizing apomorphine-induced behavior in the rat.[16] The corresponding iodo analogue, epidepride (12), with log P 1.92 is the most potent benzamide ligand known ($K_D$ 0.024 nM) for blocking the dopamine D2 receptor.[11] Interestingly, the corresponding des-3-O-methyl analogue of isoremoxipride (29) displayed a log $k_W$ value of 1.92 very similar to that of isoremoxipride despite its lack of ability to form an intramolecular hydrogen bond with the amide. The explanation for this result can be found in comparing the corresponding calculated value (1.94) which suggests that in this position, the combined cross-interactions are able to disguise the phenolic character of the hydroxy group. Of the iodine substituted benzamides, epidepride (12), its corresponding 2-ethoxy analogue (25), IBF (81), and ioxipride (36) stand out as examples of substituted benzamides which combine a moderate apparent lipophilicity (log $P_{app}$<2.5) with a lipophilic substituent in the aromatic 5-position.

Figure 3:
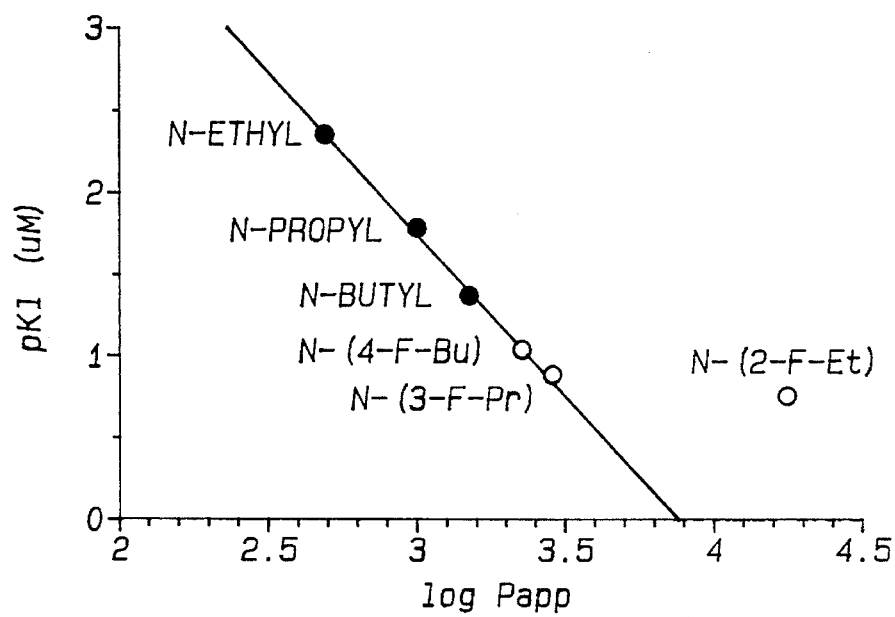

The N-(ω-fluoroalkyl) benzamides (59,60,63,64,70,71, 72) were considerably more lipophilic than would be predicted from the combined influence of a fluorine atom and an alkyl group, with fluorethyl being the most lipophilic compound. One explanation could be that fluoroalkylation reduces the basicity of the tertiary amine. Reifenrath found that N-fluoroethyl substitution of the narcotic analgetics meperidine and metacozine lowered their $pK_a$ values by 1.6 and 1.1, respectively.[45] The reverse rank order of affinity and brain uptake with increased chain length can be the result of a parabolic relationship. However, by plotting the receptor affinity ($\log(1/K_i)$) versus the apparent lipophilicity ($\log P_{app}$), it is evident that the fluoropropyl derivative (71) is the most potent fluorinated ligand because it is least lipophilic (FIG. 3). This relationship might also explain why the N-[$^{18}$F]fluoroalkyl derivatives (70,72) of raclopride and eticlopride are such poor imaging agents. Kieswetter found the striatum-to-cerebellum uptake ratio in the rat after 1 h with the fluorine-18 labelled derivatives 70 and 72 to be 1.1 and 1.6, respectively.[46]

Determination of the apparent lipophilicity, $\log k_w$, of a large series of 3- and 5-alkyl, alkoxy, and halogen substituted 2-alkoxy-N-[(1-alkyl-2-pyrrolidinyl)methyl] benzamides and their corresponding 6-hydroxy analogues has established a statistically significant data base for quantitative understanding of the substituent effects on the global octanol/water partition, log P. The two intramolecular hydrogen bonds play a dominant in the global apparent lipophilicity. Therefore, the hydroxy (salicylamide) and deshydroxy (orthopramide) series must be considered separately. A 6-hydroxy group increased the lipophilicity, in particular in the 5-alkyl series where the increase was close to one log P unit, while a 3-methoxy group decreased lipophilicity. replacement of a bromo substituent with an iodine atom, or of the methoxy groups with a fluoroethoxy group caused little or no change in lipophilicity. Substitution of an alkyl group with a fluoroalkyl group caused an increase in lipophilicity in the nitrogen 1-pyrrolidine position, in contrast to that seen when substituted in the aromatic 5-position. For fluorine in the β-position of the N-alkyl group the increase was 1.5 log P units and in the γ-position it was 0.5 units. Since radioligands with potential utility as imaging agents of the dopamine D2 receptor require relatively low lipophilic characteristics in order to display high contrast and low nonspecific binding,[7] fluoroalkylation of the tertiary amine moiety seems undesirable. Only substituted benzamides equipped with aromatic substituents such as 3-methoxy, 2-methoxy or 2-(2-fluoroethoxy) and 5-iodo or 5-(3-fluoropropyl) would be suitable for exploration as potential ligands, provided they also meet the requirement of having high affinity for the D2 receptor.

EXAMPLE 2

Radioiodination by Method A

The following is an example of the preparation of [$^{123}$I]-(S)-N-[(1-Ethyl-2-pyrrolidinyl)methyl]-5-iodo-2,3-dimethoxybenzamide by radioiodination of a trialkyltin derivative.

To a solution of [$^{123}$I]NaI(34.8 mCi, Medi-Physics) in 0.76 ml 0.1N NaOH was added 0.2 mM NaI (0.025 ml, 5.0 nmol) followed by 1.7 mM (S)-5-(tri-n-butyltin)-N-[(1-ethyl-2-pyrrolidinyl)methyl]-2,3-dimethoxybenzamide (0.025 mL, 43 nmol), made by dissolving 50 mg of the trialkyl-substituted tinbenzamide in 50 ml EtOH. Concentrated HCl (0.025 mL, 0.30 mmol) was added at 23° C. An aqueous 2 mM solution of N-chloro-4-toluenesulfonamide sodium monohydrate, Chloramine-T (0.025 mL, 50 nmol), freshly prepared by dissolving 13 mg in 25 mL sterile water, was added. After 2 minutes, 0.1M sodium metabisulfite (0.025 mL, 2500 nmol) prepared by dissolving 96 mg $Na_2S_2O_5$ in 5 mL sterile water, was added. The reaction mixture was neutralized by addition of 14 N NH4OH (0.050 mL, 0.7 mmol) and the product was extracted with ether (2×0.3 mL), the organic layer being removed with a Pasteur pipet. The combined extracts contained 32.5 mCi (86%, decay corrected). The solvent was removed with a gentle stream of nitrogen and replaced with 0.05 mL of ethanol. Purification on reverse phase HPLC gave 23 mCi (66%) of pure title compound in 5.5 mL of buffer at 17–20 min retention time at a flow rate of 2.0 mL/min. Comparison of the UV peak at 235 nm of 4.2 ug (10 nmol) of unlabelled epidepride showed peak area corresponding to 7.1 nmol of product giving a specific radioactivity of 2670 Ci/mmol at 3.5 h after synthesis. Radiochemical purity >98%. By the same method, the following radioiodinated benzamides of the present invention were synthesized from the corresponding organotin-benzamides: compound; radiochemical yield; specific activity; radiochemical purity.

[$^{125}$I]-(S)-N-[(1-Ethyl-2-pyrrolidinyl)methyl]-5-iodo-2-ethoxy-3-methoxy; 55%; 2000 Ci/mmol;>95%

[$^{125}$I]-(S)-N-[(1-Ethyl-2-pyrrolidinyl)methyl]-5-iodo-2-methoxybenzamide; 70%; 2000 Ci/mmol;>95%

EXAMPLE 3

Radioiodination by Method B

The following is an example of the alternative method of [$^{125}$I]-(S)-N-[1-ethyl-2-pyrrolidinyl)methyl]-3-iodo-5,6-dimethoxy-salicylamide by radioiodination of the corresponding desiodo derivative.

A solution of (S)-5-Chloro-N-[1-ethyl-2-pyrrolidinyl)methyl]-6-methoxysalicylamide [Hogberg, T. et al., *J. Med. Chem.*, 33; 1155–63 (1990)] (9.4 μg, 30 nmol) in ethanol (30 μL) was mixed with a solution of 10 mCi of $Na^{125}I$ (4.5 μg, 330 Ci/mmol, 30 nmol) in 0.001 N NaOH (30 μL). A solution of Chloramine-T (13 μg, 50 nmol) in water (10 μL) was added. The mixture was heated to 60° C. for 15 min. Addition of 0.1 N $NH_4Cl$ (100 μL) and extraction with ether (2×150 μl) gave 7.6 mCi of product. Thin-layer chromatography ($SiO_2$, Merck $F_{254}$) in isopropylether-methanol-concentrated $NH_4OH$ (160:39:1) showed radioactivity at $R_f$ 0.16, identical to that of an authentic sample. The product had a specific activity of 2200 Ci/mmol, radiochemical yield of 72%, and radiochemical purity >96%.

EXAMPLE 4

Synthesis of Trialkyltin Intermediates

The following is an example of the preparation of (S)-5-(tri-n-butyltin)-N-[(ethyl-2-pyrrolidinyl)methyl]-2,3-dimethoxybenzamide.

To a solution of (S)-N-[(1-ethyl-2-pyrrolidinyl methyl]-5-iodo-2,3-dimethoxybenzamide (0.42 g, 1.0 mmol) in dry Et3N (20 mL) was added solid (Ph3P)4Pd(0.06 g, 0.05 mmol) followed by Bu6Sn2 (0.58 g, 1.0 mmol). The mixture was heated to reflux temperature (bath 87° C.) for 3.5 hours. After cooling, the solvent was removed by evaporation and the residual oil (0.84 g) was subjected to chromatographic separation on silica gel to give 0.46 g (79%) of (S)-5-(tri-n-butyltin)-N-[(1-ethyl-2-pyrrolidinyl) methyl]-2,3-dimethoxybenzamide. $^1$H-NMR: δ8.62(b, NH), 7.74 (d,1,J= 0.9 Hz,H-6), 7.12 (d,1,J=0.9 Hz,H-4), 3.98 (s,3,OMe), 3.91 (s,3,OMe), 3.8–1.6 (m,11,pyrrolidinyl), 1.54 (t,6,1-Bu), 1.29 (dt,12,2+3-Bu), 1.08 (t,3,N-Et), 0.89 (t,9,4-Bu) ppm.

By the same method, the following organotin benzamides of the present invention were synthesized from the corresponding bromo or iodobenzamides: compound; Rf (solvent); NMR data; starting derivative.

(S)-(–)-N-[1-Ethyl-2-pyrrolidinyl) methyl]-5,6-dimethoxy-3-tri-n-butyltinsalicylamide; Rf 0.58 (isopropylether-methanol-concentrated ammonium hydroxide (160:39:1)); δ7.08 (s,1H), 3.93 (s,3H), 3.84 (s,3H) ppm; bromo derivative.

(S)-(−)-N-[(1-Ethyl-2-pyrrolidinyl) methyl]-2-methoxy-5-tri-n-butyltinbenzamide; Rf 0.32 (isopropylether-methanol-concentrated ammonium hydroxide (160:39:1)); δ8.26 ppm (d,J=3 Hz, C6-H); iodo derivative.

(S)-(−)-N-[(1-Ethyl-2-pyrrolidinyl) methyl]-2-ethoxy-5-tri-n-butyltin-3-methoxybenzamide; Rf 0.43 (isopropylether-methanol-concentrated ammonium hydroxide (160:39:1)); δ7.74 ppm (d,J=0.9 Hz, C6-H) and 7.12 ppm (d,J=0.9 Hz, C4-H) bromo derivative.

(S)-(−)-N-[(1-Ethyl-2-pyrrolidinyl) methyl]-2,3-dimethoxy-5-(tri-n-butyltin) benzamide; Rf 0.56 (isopropylether-methanol-concentrated ammonium hydroxide (160:39:1)); δ 7.74 ppm (d,1,J=0.9 Hz,H-6), 7.12 ppm (d,1,J=0.9 Hz, H4); bromo derivative.

EXAMPLE 5

This example characterizes the in vitro binding of [$^{125}$I] epidepride to striatal, cortical and limbic regions. In vitro autoradiography was performed to access its utility in imaging limbic and cortical receptors. In vivo studies of [$^{125}$I] epidepride uptake in frontal cortex and hippocampus were performed to evaluate its utility for the in vivo study of extrastriatal dopamine D2 receptors.

Receptor Binding Studies

Male Harlan-Sprague-Dawley rats (200-350 g) were sacrificed, the brain removed and regionally dissected on an ice cold porcelain dish into striatum, cerebellum, hippocampus and frontal cortex. The tissue was stored at −80° C. unless used on the day of sacrifice. On the day of assay each region was homogenized, using a Brinkman Polytron (15 seconds at half maximum speed), in a 100 fold (w:v) dilution of 50 mM Tris HCl buffer, Ph 7.4, containing 120 mM NaCl, 5 mM, KCl, 2 mM CaCl$_2$, 1 mMMgCl$_2$, 1 mM NaEDTA, and 0.1 mM Na ascorbate. The homogenate was centrifuged at 12,000× g for 15 minutes at 4° C., resuspended in the same volume of buffer, recentrifuged, and resuspended in buffer at 500 dilution (w:v) for the striatum and 100 (w:v) dilution for cortex, hippocampus and cerebellum. For assays measuring ion requirements, the buffer modified as indicated below. To start the incubation, 0.5 ml of the tissue homogenate was added to ice cold assay tubes containing appropriate concentration of radioligand in a final volume of 2 ml. Following addition if tissue, the tubes were removed from the ice, vortexed for 3 seconds, and incubated at 25° C. for 240 minutes. Incubation was terminated by filtration through Whatman GF/B filters, presoaked in 0.3% polyethylenimide, using a Brandel model M-24R cell harvester. The filters were rinsed for 10 seconds with ice cold Tris HCl buffer and the filter placed in a gamma counting tube. Gamma spectrometry was performed with an LKB model 1282 Universal Compugamma CS instrument.

Tissue and the [$^{125}$I] epidepride ligand solutions for determination of Na$^+$ requirements were prepared in sodium free 50 mM Tris HCl buffer. Final Na$^+$ concentrations of 0, 20, 40, 80, 120, 160 and 200 mM were utilized. Assays were performed as detailed above. Nonspecific binding (in this and all subsequent binding assays) was estimated using 10 μM sulpiride. For determination of Ca$^{2+}$, Mg$^{2+}$, and K$^+$ requirements, the incubation buffer contained 120 mM Na+; Ca$^{2+}$ or Mg$^{2+}$ or K$^+$ was added to achieve final concentrations ranging from 0 to 10 mM.

Using optimal ionic requirements as determined above, specific binding to a range of striatal tissue concentrations were assayed. Tissue dilutions of 1:50, 1:100, 1:200; 1:500, 1:1000, and 1:2000 (w:v) were incubated with 25 pM [$^{125}$I]epidepride.

Using the appropriate concentration of striatal tissue homogenate and optimal ion concentrations of [$^{125}$I]epidepride binding assays were performed at 4° C., 25° C., 30° C., and 37° C. for 20, 40, 80, 160, 200, 220, 240, 260, 280, 300, 320 and 340 minutes.

Using optimal conditions as determined above, specific binding of [$^{125}$I]epidepride at 12 concentrations, from 0,001 to 1 nM, were determined. Scatchard analysis of binding data from striatum, hippocampus, medial frontal cortex, and cerebellum was performed.

To determine the IC$_{50}$'s for displacement of [$^{125}$I]epidepride from striatal, medial frontal cortical, and hippocampal homogenates by various neurotransmitter receptor ligands, the specific binding of [$^{125}$I] epidepride (50 pM) at eleven concentrations (0 to 100,000 nM) of these ligands were measured in duplicate; nonspecific binding was determined using 10 μM sulpiride.

In Vivo Studies

Groups of four 200–250 gram male Harlan-Sprague-Dawley rats were injected via tail vein with 25 μCi of [$^{125}$I]epidepride (specific activity>500 Ci/mmol). Groups of rats were sacrificed at 5, 20, 40, 80, 160 and 320 minutes after injection. The brain was rapidly removed, washed in iced saline, dissected, the medial frontal cortex, hippocampus and cerebellum removed, weighed and gamma spectrometry performed.

A separate group of four rats received 2 mg/kg haloperidol intraperitoneally 60 minutes prior to the injection of 25 μCi [$^{125}$I] epidepride and were sacrificed at 80 minutes following [$^{125}$I]epidepride injection. Regional brain dissection and gamma spectrometry was performed as described above.

Autoradiographic Studies

Six male Sprague-Dawley rats (250–300 g) were euthanized with an overdose of chloral hydrate. Brains were rapidly removed, mounted on chucks, and frozen on powdered dry ice. Coronal cryostat sections (20 μm thick) were collected from prefrontal and cingulate cortices, thaw-mounted onto gelatin-coated glass slides, and stored at −20° C. until use. Prior to assay, sections were thawed at room temperature and then placed on staining racks in a covered moist environment.

Slide-mounted tissues were incubated at room temperature for 2 hours with approximately 10 pM [$^{125}$I]epidepride (specific activity 2000 Ci/mmol) in 50 mM Tris-HCl buffer, pH 7.4, containing 120 mM NaCl, 5 mM KCl, 2 mM CaCl$_2$. After incubation, the slides were washed twice for 5 minutes each in ice cold buffer, followed by a quick dip in distilled water before drying in a stream of cold air. Nonspecific binding was determined by incubation with 1 μM (+)-butaclamol.

After drying, sections were apposed to autoradiographic film (LKB Ultrafilm) along with $^{125}$I standards ($^{125}$I-microscales, Amersham), and stored in light-tight cassettes at 20° C. Exposure times for the autoradiograms were approximately 10 days for cortical regions and 3 days for striatal regions. Film was developed with Kodak D-19. The distribution of receptors was quantified in three autoradiograms from each six animals using computerized microdensitometry (Amersham RAS 1000 Image Analysis System) relative to $^{125}$I standards. Adjacent sections were stained with cresol violet for precise anatomic localizations.

RESULTS OF EXAMPLE 5

Figure 4A:
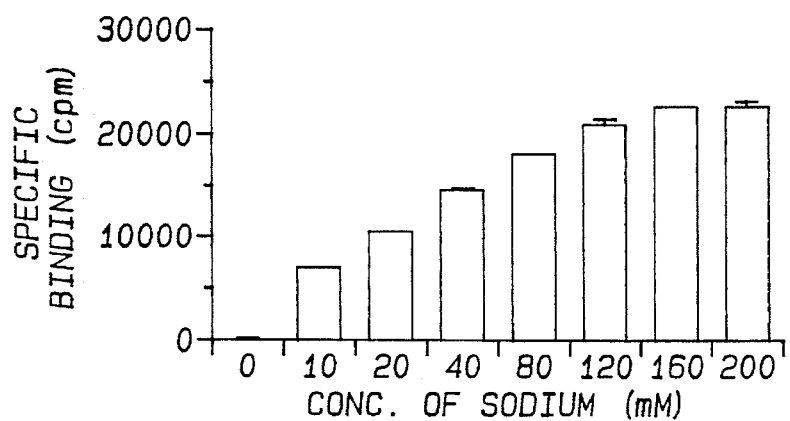
FIG. 4 shows the effect of cations on the specific binding of [$^{125}$I]epidepride to rat striatal homogenate: (A)NaCl, (B)KCl, (C)MgCl$_2$, (D)CaCl$_2$.
Figure 4B:
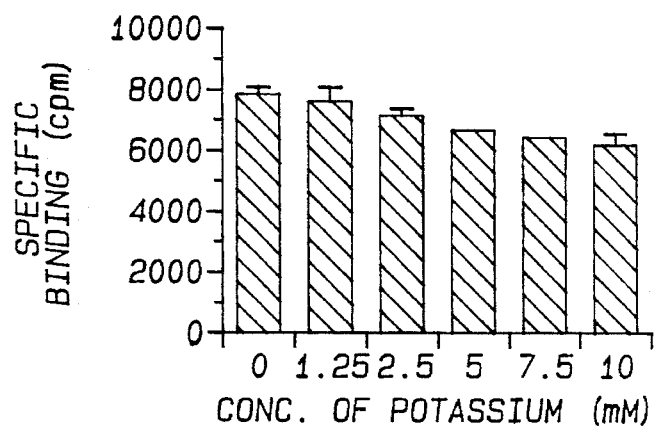
Figure 4C:
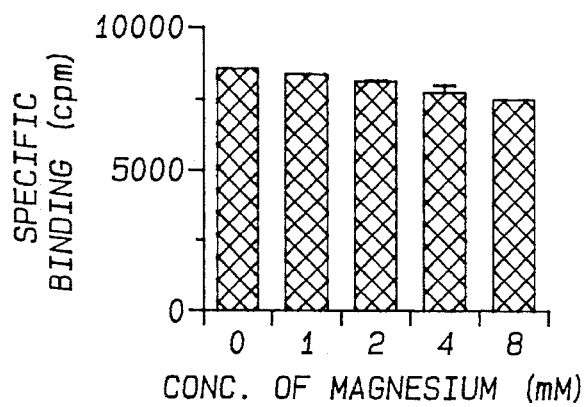
Figure 4D:
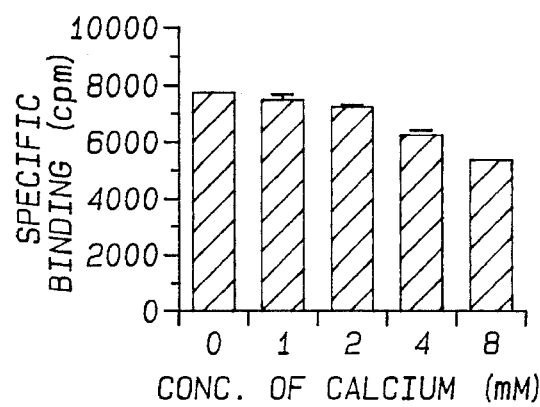

As found with other substituted benzamides, optimal specific binding of $^{125}$I]epidepride to dopamine D2 receptor required the presence of sodium. FIG. 4A shows up to 120 mM; above that level there was a gradual 13% increase in binding at concentrations up to 200 mM. Potassium appeared to produce a mildly inhibitory effect on [$^{125}$I]

epideride binding, with a 20% inhibition of specific binding evident at a concentration of 10 mM (FIG. 4B). Magnesium and calcium ions had little effect on specific binding at concentrations of 1 or 2 mM; mild inhibition of binding was seen at 4 mM (FIGS. 4C and 4D). All subsequent assays were performed using 120 mM NaCl, 5 mM KCl, 2 mM $CaCl_2$ and 1 mM $MgCl_2$. Specific binding to striatal homogenates was linear over the entire range of tissue concentrations from 0.1 mg/ml (1:2500 w:v) to 2.5 mg/ml (1:50 w:v). Subsequent assays were performed at a 1:500 w:v dilution for striatal homogenates and a 1:100 w:v dilution for other brain regions.

Figure 5:
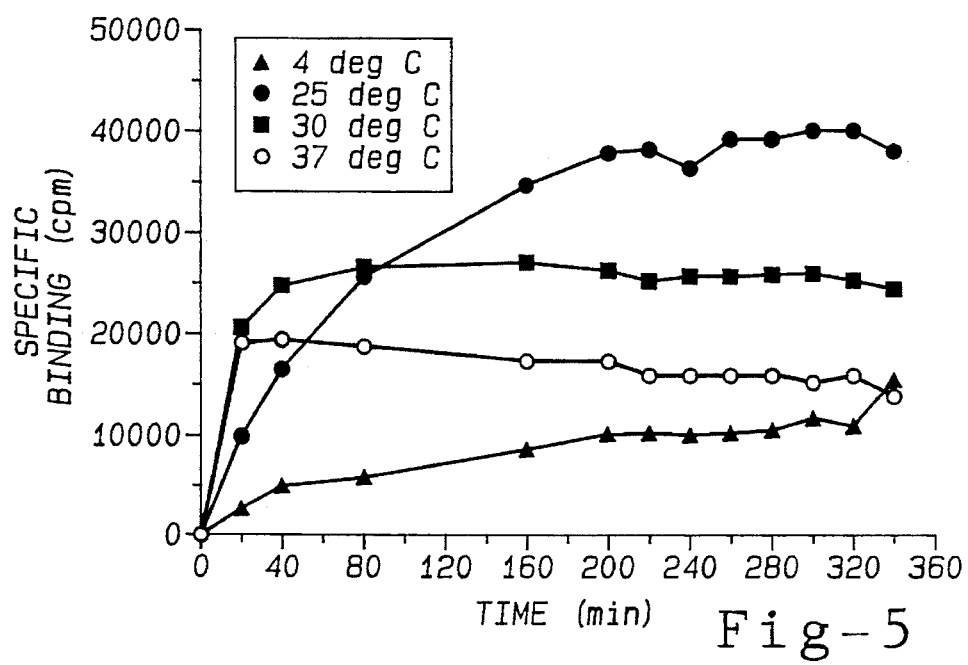
FIG. 5 shows the effect of incubation time and temperature on specific binding of [$^{125}$I] epidepride to striatal homogenate in Tris buffer (pH 7.4) containing 120 mM NaCl, 5 mM KCl, 2 mM CaCl$_2$.

The effect of time and temperature on specific binding to striatal homogenates is shown in FIG. 5. Maximal specific binding was seen at 25° C. at an incubation time of 240 minutes. At 30° C. and 37° C. maximal binding was reached at 80 and 120 minutes, respectively, but the level of binding was only two-thirds and one-half, respectively, of that observed at 25° C. Maximum binding at 4° C. was not reached after 320 minutes. All subsequent binding studies were performed at 25° C. using an incubation time of 240 minutes.

Figure 6:
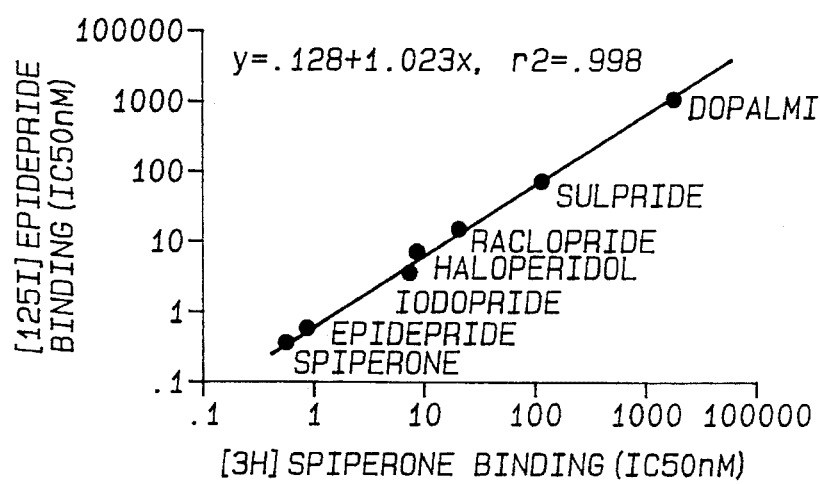
FIG. 6 shows a correlation of the inhibition of [$^3$H] spiperone binding with the inhibition of [$^{125}$I]epidepride binding to rat striatal homogenate for selected dopamine D2 ligands. Correlation coefficient is 0.999.
Figure 7A:
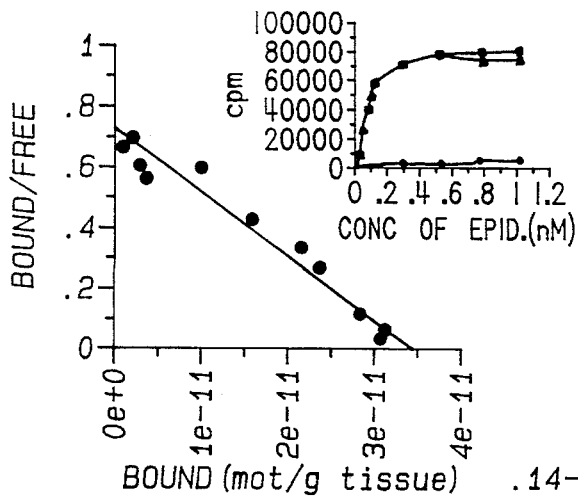
Figure 7B:
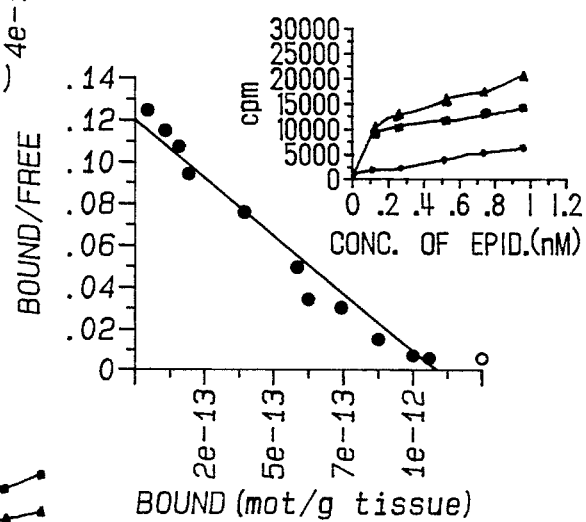
Figure 7C:
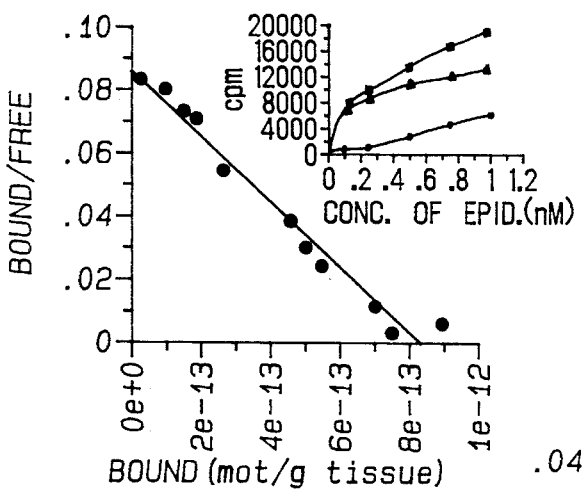
Figure 7D:
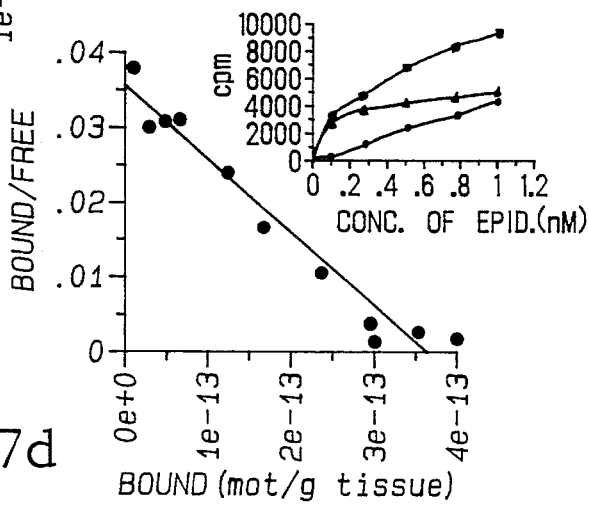

Correlation of $IC_{50}$'s for inhibition of [$^3$H]spiperone binding to striatal membranes with the $IC_{50}$'s for inhibition of [$^{125}$I]epideride binding to striatal membranes for several known D2 ligands reveals a correlation coefficient of 0.99, indicating that the striatal epideride binding site is a dopamine D2 receptor (see FIG. 6).

Using optimal binding conditions, Scatchard analysis of binding to striatal, frontal cortical, hippocampal, and cerebellar homogenates gave the following $K_D$'s (pM) and $B_{max}$'s (pmol/g wet weight): 24.4 and 36.7 in the striatum, 24.0 and 1.04 in the medial frontal cortex, 24.1 and 0.85 in the hippocampus and 24.4 and 0.37 in the cerebellum. FIG. 7 shows representative saturation and Scatchard plots of binding in these four regions. Of note are the low levels of nonspecific binding, even in regions with low receptor density. At ligand concentration approximating the $K_D$, i.e. 25 pM, nonspecific binding was only 10%, 5%, 5% and 1% of total binding in cerebellar, hippocampal, frontal cortical and striatal homogenates, respectively. Using 10 µM sulpiride to define nonspecific binding, the Hill coefficients ranged from 0.91 to 1.00 for the tissues studied.

As can be seen in Table 7, a variety of serotonergic, noradrenergic, GABAergic, cholinergic, and opiate receptor ligands showed limited ability to displace [$^{125}$I]epideride. The selective dopamine D1 receptor ligands SCH 23390 (36) and SKF 83566 (37) demonstrated low potency for displacing [$^{125}$I]epideride as well. Only ligands with high affinity for the dopamine D2 receptors demonstrated high potency as displacing [$^{125}$I]epideride in all regions studied.

Careful examination of the displacement curves for the ligands shown in Table 7 revealed a partial displacement of frontal cortical and hippocampal [$^{125}$I]epideride specific binding by nanomolar concentrations of clonidine, while no displacement of [$^{125}$I]epideride binding was seen in the striatum. This suggested binding to an noradrenergic $\alpha_2$ binding site in frontal cortex and hippocampus. Accordingly, Scatchard analysis of [$^{125}$I]epideride binding to noradrenergic $\alpha_2$ receptors in frontal cortical and hippocampal homogenates was estimated by using 1 µM clonidine to define nonspecific binding. This analysis revealed a an apparent $K_D$ for the $\alpha_2$ receptor of 8.8 nM in the frontal cortex and 10.2 nM in the hippocampus, with $B_{max}$'s of 11.2 and 9.2 pmol/g tissue respectively. Hill coefficients were 0.84 and 0.93, respectively. Thus, there is more than a 350 fold D2/$\alpha_2$ selectivity for epideride binding. For binding studies of the dopamine D2 receptor performed at the $K_D$ of epideride for the D2 receptor, i.e. 25 pM, only 7% of frontal cortical or hippocampal binding was due to binding at the $\alpha_2$ site. At 10 fold higher concentration, i.e. 0.25 nM, 22% of specific frontal cortical binding was due to binding at the $\alpha_2$ receptor.

Time activity curves of in vivo uptake of [$^{125}$I]epideride in rat brain medial frontal cortex, hippocampus and cerebellum are shown in FIG. 8. The peak uptake ratio of medial frontal cortex or hippocampus to cerebellum was 2.2:1 at 80 minutes following injection. At this time 0.046 and 0.047% of administered dose per gram tissue were seen in hippocampus and prefrontal cortex. The uptake rations of medial frontal cortex and hippocampus to cerebellum fell to 1.1:1 following haloperidol pretreatment (mg/kg i.p.), suggesting binding to dopamine D2 receptors in these regions. It should be that the in vitro ratios of frontal cortical and hippocampal to cerebellar receptor concentrations for the D2 receptor are approximately 2.8 and 2.3. The similarity of these ratios, i.e. in vivo uptake and in vitro receptor density, indicates that the cerebellum is not an appropriate "blank" for imaging studies of limbic and cortical D2 receptors.

Autoradiograms prepared with [$^{125}$I]epideride showed clear localization of binding sites in striatum and deep layers (V and VI) of rat prefrontal and cingulate cortices (FIG. 9). Nonspecific binding was almost invisible to the naked eye and had optical densities approximately equal to that of adjacent film not apposed to tissue sections. At a radioligand concentration of approximately 10 pM, the density of binding sites were: striatum, 190±10; cingulate layers I–VI, 9±1; and cingulate layers V–VI, 16±1 fmol/g tissue, with data expressed as mean ± SEM from regions determined bilaterally from two autoradiograms from each of four animals. These studies are consistent with homogenate binding studies of rat cortex performed with [$^3$H]raclopride (19), the distribution of dopamine fibers in the deeper layers of prefrontal and supragenual cingulate cortices and previous autoradiographic studies of dopamine D2 receptors in rat brain.

This study demonstrates that epideride is a very potent and selective dopamine D2 receptor ligand ($K_D$24pM), with very low nonspecific binding. It can be prepared at high specific activity (>2,000 Ci/mmol) with [$^{125}$I]radiolabelling. The low nonspecific binding is presumably related to the relatively low apparent lipophilicity of epideride [(log $k_W$2.05 at pH 7.5) (40)]. This combination of properties allows Scatchard analysis of in vitro binding to dopamine D2 receptors in regions with low receptor density, i.e. cortex, hippocampus and even in the cerebellum. While epideride has some affinity for the $\alpha_2$ noradrenergic receptor, its greater than 350 fold selectivity for the D2 dopamine versus $\alpha_2$ receptor allows selective labelling of the D2 site when studies are performed at concentrations of epideride near it $K_D$ for the D2 receptor, (i.e. 24 pM). Other benzamides have affinity for $\alpha_2$ and $\alpha_1$ noradrenergic receptors as well. Hall and colleagues (41) have reported selectivity ratios of 65:1 for D2/$\alpha_2$ binding for sulpiride, 10:1 D2/$\alpha_2$ for remoxipride, and 122:1 for D2/$\alpha_1$ for eticlopride. Affinity for the $\alpha_2$ receptor was noted. The $K_D$ of epideride for the $V8,1_2$ receptor, approximately 9 nM, was measured using equilibrium binding techniques and Scatchard analysis. The highest concentration used in this study was considerably below the calculated $K_D$ for the $\alpha_2$ site and may be regarded as an approximation.

The autoradiographic data clearly delineates D2 receptors in the deeper layers of frontal cortex and pregenual cingulate. This is consistent with the distribution of dopamine fibers in the deeper layers of the prefrontal cortex and supragenual cingulate cortex.

In comparing [$^{125}$I]epidepride to other highly potent benzamide ligands for the D2 receptor, it is important to analyze the factors responsible for its ability to delineate the very low levels of D2 receptors in extrastriatal tissues by in vitro binding assays, autoradiography and in vivo studies. In an equilibrium binding assay with a given receptor concentration and a ligand concentration below saturation, the fraction of specifically bound ligand is a function of the ligand affinity. Nonspecific binding may be assumed to be related to lipophilicity. Thus, high ratios of specific to nonspecifically bound and free ligand, needed to detect low receptor concentrations; require both high affinity and low lipophilicity. Both high affinity and moderate lipophilicity are needed to achieve high contrast between striatum and cerebellum for in vivo uptake in rat brain. Epidepride is not only an extremely potent D2 receptor ligand, but also has moderate lipophilicity (log $k_W$ 2.05). In comparison, emonapride, eticlopride, IBF, and ioxipride (NCQ 298) all demonstrate either higher lipophilicity and/or lower potency at the D2 receptor. IBF, for example, has a $K_D$ 106 pM and a log $k_W$ of 2.32 indicating a four-fold lower potency and a nearly two-fold higher lipophilicity. Ioxipride (NCQ 298) has a potency equal to that of epidepride but a log $k_W$ of 2.48 indicating that it is about three-fold more lipophilic than epidepride; in vivo rat studies showed a 3.6 fold higher striatal: cerebellar ration for epidepride (234:1) than ioxipride (65:1) consistent with the difference in lipophilicity. Similarly, eticlopride with a $K_D$ of 90 pM and a log $k_W$ of 3.27 shows higher nonspecific binding than epidepride with in vitro equilibrium binding studies, lower in vivo striatal-:cerebellar contrast (10:1 versus 234:1), and an inability to delineate cortical D2 receptors seen with epidepride. Thus the combination of high affinity for the D2 receptor and relatively low lipophilicity as well as the ability to radiolabel [$^{125}$I]epidepride to high specific activity (2000 Ci/mmol) makes epidepride a superior ligand for the in vitro and in vivo study of the dopamine D2 receptor.

In summary, a combination of very high affinity and selectivity for the dopamine D2 receptor, very low nonspecific binding, and the capability of radiolabelling to a high specific activity (2,000 Ci/mmol) combine to make $^{125}$I labelled epidepride a superior ligand for the in vitro and autoradiographic study of cortical, limbic and striatal dopamine D2 receptors. In addition, these results indicate that $^{123}$I labelled epidepride would be a superior candidate ligand for single photon tomographic imaging of the dopamine D2 receptor in man.

EXAMPLE 6

This example demonstrates which substituted iodinated benzamides might be suitable as potential D2 ligands for single emission tomography (SPECT) and evaluates the relationship of receptor affinity and lipophilicity to the regional brain uptake of these tracers. The compounds evaluated include iodopride, iclopride, ioxipride, and epidepride. A preliminary evaluation of itopride, a substituted benzamide structurally related to eticlopride, was also performed.

METHODS

In Vitro Receptor Binding Studies

Male Harlan-Sprague-Dawley rats (200–300 g) were sacrificed, the brain removed, dissected and striatum stored at −80° C. if not used on the day of sacrifice. On the day of assay, the striatum was homogenized using a Brinkman Polytron (15 seconds at half-maximum speed) in a 100-fold (w:v) dilution of a 50-mM KCl, 2 mM CaCl$_2$, 1 mMMgSO$_4$, 1 mM NaEDTA, and 100 µM Na ascorbate. The homogenate was centrifuged at 10,000×g for 15 minutes at 4° C., the pellet resuspended in the same volume of buffer, centrifuged a second time, and resuspended in fresh buffer at 500 w:v.

The IC50 for inhibition of [$^3$H]spiperone binding to striatal homogenate was determined as follows. Prior to incubation, the assay tues were placed on ice and the assay started by addition of 0.5 ml of the tissue homogenate to each tube containing [$^3$H] spiperone (at a final concentration of 300 pM), 10 nM ketanserin, 10 µM pargyline, and the displacing ligand at a final concentration of from 0.001 to 100,000 nM with a final volume of 2 ml. Nonspecific binding was determined using a concentration of 10 µM spiperone. Each tube was removed from ice, vortexed for 3 seconds, and incubated at 25° C. for 50 minutes. Incubation was terminated by filtration through Whatman GF/B filters presoaked in 0.3% polyethylenimine, using a Brandel model M-24R cell harvester. The filters were rinsed for 10 seconds with ice-cold Tris HCl buffer, the filter placed in a 20 ml plastic scintillation vial and 10 ml of scintillation fluid was added. Liquid scintillation counting was performed using a Beckman LS3801 counter; efficiency was typically 45%.

The $K_D$ for ligand binding to striatal homogenates was determined as follows. If frozen, the tissue was thawed, homogenized at 100-fold dilution (w:v) in a Tris-HCl buffer for 15 seconds using a Brinkman Polytron at half-maximum speed. The homogenate was centrifuged at 4° C. at 10,000× g for 15 minutes, the supernatant discarded, the pellet resuspended in the initial volume of fresh buffer, and centrifuged a second time. The supernatant was again discarded and the pellet resuspended in a Tris-HCl buffer containing 50 mM Tris pH 7.4, 120 mM NaCl, 2 mM CaCl$_2$, 1 mMMgSo$_4$, 1 mM NaEDTA, and 100 µM Na ascorbate at a final dilution of 500 w:v. Incubation was performed in duplicate in a total of 2.0 ml Tris-HCl-Na buffer containing 0.5 ml tissue and 20 µl radioactive ligand (final concentration 0.0001 nM to 500 nM). The tissue was incubated for 45 minutes at 25 ° C. and the binding assay terminated by filtration as described above. The filter was placed in a gamma counting tube and gamma spectrometry performed using a Searle Analytic Inc model 1185, with 86% efficiency. Nonspecific binding was determined by adding 10 µM sulpiride to the incubation mixture.

In Vivo Studies

Groups of four 200–250 g male Harlan-Sprague-Dawley rats were injected with 25 or 30 µCi of $^{125}$I labelled iodobenzamide via tail vein. The animals were killed at 5, 20, 40, 80, 160 and when necessary, 320, 640 and 1,280 minutes after injection. The brains were rapidly removed, washed in iced saline, regional brain dissection was performed, and the cerebellum and striatum were weighed and counted using gamma spectrometry.

To assess to effect of haloperidol, 2 mg/kg haloperidol was administered intraperitoneally 60 minutes prior to the tail vein administration of 25 or 30 µCi $^{125}$I-labelled iodobenzamide. Groups of four rats were killed at 60 minutes after [$^{125}$I]iodopride or [$^{125}$I]iclopride injection, or 80 minutes after injection of [$^{125}$I]epidepride or [$^{125}$I]ioxipride.

To assess in vivo displacement of epidepride,groups of four 200–250 g Sprague-Dawley male rats were injected with 25 µCi [$^{125}$I]epidepride via tail vein injection and 40 minutes later received either 5 mg/kg haloperidol or saline also via tail vein injection . Groups of four rats were killed at 40, 80, 160, and 320 minutes post-haloperidol injection, brain regions dissected, and tissues counted as described above.

To demonstrate receptor saturation, groups of three or four rats were injected with 25 μCi of [$^{125}$I]epidepride or of 30 μCi of [$^{125}$I]iodopride. Increasing doses of unlabeled ligand were used to attain specific activities of 100, 50, 20, 10, 5, 2, 1, and 0.2 Ci/mmol. The animals were killed at either 60 minutes or 80 minutes post-injection, depending upon whether iodopride or epidepride was utilized. After sacrifice, the brains were dissected and counted as described.

RESULTS OF EXAMPLE 6

In Vitro Binding

The IC$_{50}$s for inhibition of [$^3$H]spiperone binding to striatal membranes, the log k$_W$ at pH 7.5, and the K$_D$s for binding to striatal membranes for the iodine substituted benzamides and reference compounds are shown in Table 8. Iodopride is a structural analogue of sulpiride, having an iodine atom substituted for the aminosulfonyl group in the five-position of the aromatic ring. It has an IC$_{50}$ of 10.2 nM and a K$_D$ of 0.88 nM. Iclopride and itopride are structural analogues of eticlopride. Iclopride has an iodine atom substituted for the ethyl group in the five-position of the atom ring, while itopride has an iodine atom substituted for the chloro atom in the three-position of the aromatic ring. The IC$_{50}$s for these compounds are 8.1 nM and 1.5 nM, respectively; the K$_D$s are 0.23 nM and 0.16 nM, respectively. Epidepride and ioxipride are structural analogues of isoremoxipride. Epidepride has as iodine atom substituted for the bromine atom in the five-position at the aromatic ring of isoremoxipride. In addition, ioxipride has both an iodine in the five-position and a hydroxy group in the six-position of the aromatic ring. The IC$_{50}$s for displacing [$^3$H]spiperone are 1.02 nM for epidepride and 0.94 nM for ioxipride. Epidepride has an apparent K$_D$ for striatal membranes of 57 pM. The Hill coefficients for all five ligands ranged between 0.89 and 1.0, suggesting that all bind to a single site in striatal membranes.

In Vivo Regional Brain Uptake

Plots of time-dependent in vivo regional brain uptake for $^{125}$I-labelled iodopride, iclopride, ioxipride, and epidepride are shown in FIG. 10. Iodopride and iclopride have peak striatal:cerebellar ratios of 7.6:1 and 9.8:1 at 80 minutes after injection, respectively. Both show rapid washout from the striatum so that little radioactivity is seen by 160 minutes. Peak uptake is seen at 20 minutes after injection, at which time uptake of iodopride and iclopride are 0.76 and 0.44%/g of striatum, respectively. Iotopride has a peak striatal:cerebellar ration 3.3:1 at 320 minutes post-injection and a peak striatal uptake of 0.35% g. Of note are the high peak striatal:cerebellar ratios obtained for ioxipride and epidepride, 65:1 and 234:1, respectively, at 640 minutes after injection and the relatively stable striatal levels of these two compounds. Striatal levels of ioxipride vary less than 22% from 20 minutes to 160 minutes after injection, at which time a striatal:cerebellar ration of 188:1 is seen. The percent of administered dose seen in both striatum and cerebellum was considerably higher for ioxipride than for the epidepride; peak striatal uptake was 0.86%/g tissue for ioxipride and 0.49%/g tissue for epidepride.

D2 Receptor Blockade In Vivo

To estimate the proportion of striatal uptake due to D2 receptor binding, haloperidol (2 mg/kg i.p.) was give one hour prior to tail vein injection of the radioiodinated tracer. For iodopride and iclopride, rats were killed 40 minutes post-injection of tracer, while for ioxipride and epidepride rats were sacrificed at 80 minutes post-injection. The percent of blockade of striatal uptake was calculated as follows:

$$\text{percent blockade} = \frac{[(\text{striatum} - \text{cerebellum})\text{control} - (\text{striatum} - \text{cerebellum})\text{haloperidol}]}{(\text{striatum} - \text{cerebellum})\text{controlled}} \times 100,$$

where striatum and cerebellum refer to the concentrations of radioactivity in each region. The blockade of uptake was 92% for iodopride, 93% for iclopride, 98% for epidepride, and ioxipride. Thus, nearly all the radioactivity in the striatum with these tracers can be blocked by pretreatment with haloperidol.

The relatively rapid washout of iodopride and iclopride from the striatum demonstrates that these ligands are reversibly bound in vivo. The slower washout of activity seen with ioxipride and epidepride leaves some question as to the ready reversibility of epidepride binding, 25 μCi of [$^{125}$I] epidepride was injected via tail vein, and 40 minutes later either saline or haloperidol was administered intravenously. FIG. 11A shows the uptake of [$^{125}$I]epidepride in the striatum from the injection to 320 minutes post-epidepride injection. Figure lib shows the washout of [$^{125}$I]epidepride by haloperidol from the striatum for the period from 40 minutes post-epidepride injection to 320 minutes post-epidepride injection. There is a rapid and to a first approximation monoexponential washout of radioactivity from the striatus with a half-life of 40 minutes. The in vivo binding of [$^{125}$I]epidepride appears to be completely reversible.

Receptor Saturation

Figure 12B:
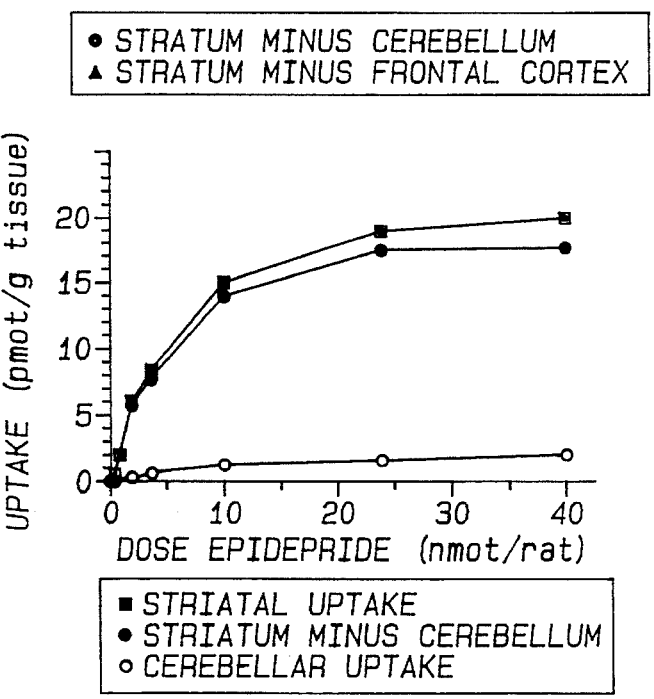

Receptor binding should be saturable in vivo. To demonstrate saturability, increasing doses of unlabeled ligand were added to 25 μCi of $^{125}$I-labelled ligand. Saturation curves were obtained for one of the lower affinity ligands, iodopride, at 60 minutes post-injection and one of the higher affinity ligands, epidepride, at 80 minutes post-injection (see FIGS. 12A and 12B). Cerebellar uptake was initially used as a measure of nonspecific binding and free ligand in striatum. Saturation could not be demonstrated for iodopride and the uptake curve (FIG. 12A) suggests that the cerebellum underestimates nonspecific binding in the striatum. When the frontal cortex was used as a measure of nonspecific binding and free ligand, saturation could be demonstrated, with B$_{max}$=26 pmol/g tissue in the striatum. This is in reasonable agreement with in vitro determinations, which found a B$_{max}$ of 35 pmol/g in striatum. In support of using the frontal cortex as opposed to the cerebellum is the observation that with haloperidol blockade, the striatal uptake fell to the level seen in the frontal cortex (within experimental error) but remained 50% higher than seen in the cerebellum. The same findings were seen with iclopride following haloperidol pretreatment. With epidepride, saturation can be demonstrated using cerebellum as measure of nonspecific binding since the levels of nonspecific binding are very low (FIG. 12B).

Relationship of In Vivo Regional Brain Uptake to Receptor Affinity and Lipophilicity With a given receptor concentration in a target issue, it has been demonstrated that the affinity of a ligand places a limit on the contrast between receptor rich and receptor poor tissues. To study the relationship of affinity for the D2 receptor to the striatal:cerebellar ratios for various benzamides, a plot of K$_A$ versus reported striatal:cerebellar was performed. This plot demonstrates only a weak correlation (r=0.35) between K$_A$ and this ratio.

Previous work on optimization of ligands for the estrogen receptors has indicated that contrast between receptor rick and receptor poor tissues is a function of both receptor affinity and nonspecific binding. To examine this hypothesis, in vivo affinity was represented by the in vitro K$_D$; nonspecific binding was assumed to be related to lipophilicity, and this was represented by the log $k_W$ at pH 7.5. The log $K_D$ (nM)+log $k_W$ (pH 7.5) was plotted against log striatal:cerebellar rations (FIG. 13) for the same compounds as above. The apparent lipophilicities, log $k_w$s, were measured in our laboratory for all ligands except emonapride (YM 09151-2) where the value reported by El Tayar was utilized. There was an excellent linear correlation (r=0.92) demonstrating that contrast between striatum and cerebellum depends on both the affinity of a ligand for the dopamine D2 receptor and its apparent lipophilicity (log $k_W$) at pH 7.5.

The image contrast, i.e., striatal:cerebellar ratio, is an important variable in imaging of D2 receptors, but total uptake in the tissue of interest, i.e. striatum is an important concern. If it is assumed that there is a passive transfer across the bloodbrain barrier, then one would expect a relationship between brain uptake and lipophilicity. A plot of striatal uptake versus log $k_W$ at pH 7.5 for the compounds studies is shown in FIG. 14. Peak uptake occurred at a log $k_W$ of about 2.4–2.8 and declined above and below that value, suggesting an inverted parabolic relationship.

The above example evaluated the affinity for the dopamine D2 receptor, lipophilicity, and in vivo rat brain distribution of four new iodinated benzamides and preliminarily evaluated a fifth.

In regard to regional brain distribution, the high striatal:cerebellar ratio seen with [$^{125}$I]epidepride in the rat (234:1) is the highest that has been reported to date. The relatively high and stable in vivo uptake of [$^{125}$I]epidepride, together with the high contrast found between dopamine-rich and dopamine-poor brain regions, make epidepride and excellent candidate radioligand for SPECT imaging. Iodine-125-ioxipride administration also results in a high striatal:cerebellar ratio (65:1) with stable striatal levels, but with. 70% higher peak striatal uptake than seen with epidepride. In a recent report, a striatal:cerebellar ratio of 15:1 3 hour post-injection of [$^{125}$I]ioxipride (NCQ 298) was obtained in cynomologous monkeys.

In comparison to currently available SPECT ligands for the D2 receptor, e.g., IBZM, IBF, 2-iodospiperone, and spectramide, the new iodobenzamides, epidepride and ioxipride, appear to be superior candidate ligands. The previously reported ligands have in vivo rodent striatal:cerebellar uptake ratios of 10:1, 48:1, 14:1, and 4:1, respectively, in comparison to 234:1 and 65:1 for epidepride and ioxipride. Ioxipride and epidepride have relatively stable striatal uptake in the rat, with the half-maximum striatal level during washout attained at 7 and 10 hours post-injection, respectively; in contrast, IBF (28) has a more rapid washout, with the half-maximum level being reached at approximately 2 hours. The $K_D$s reported here for ioxipride and epidepride are lower than those reported for the above ligands, except spectramide. Spectramide, with a reported $K_D$ of 25 pM, is clearly a very potent D2 ligand. However, like emonapride (YM 09151-2), to which it is structurally related, spectramide shows only modest in vivo contrast. The $K_D$s reported here must be regarded as preliminary, as careful optimization of binding conditions for each ligand was not performed.

The relationship between affinity, lipophilicity, and in vivo striatal:cerebellar ratios suggests that in addition to high affinity, relatively low apparent lipophilicity is crucial achieve high tissue contrast. Eticlopride, as well as its structural analogue itopride, and emonapride have high affinity for the D2 receptor. However, the relatively high log $k_W$ ($\geq 3.27$) of each compound results in relatively high levels of nonspecific binding; therefore, tissue contrast is relatively moderate (10:1, 3.3:1, and 4:1, respectively). Spectramide, being structurally related to emonapride, is presumably highly lipophilic as well, which explains its relatively low in vivo striatal:cerebellar contrast despite its high affinity for the dopamine D2 receptor. In contrast, epidepride and ioxipride both have very high affinity and relatively low lipophilicity, a combination that results in the very high in vivo contrast seen with these compounds. These compounds differ from iodopride and IBZM only by the presence of a 3-methoxy substituent. This substituent has the property of raising affinity by an order of magnitude while lowering apparent lipophilicity.

As discussed above, an inverted parabolic relationship between striatal uptake of tracer and log $k_W$ is seen. The presumed explanation for this behavior is that molecules with relatively low lipophilicity do not cross the blood-brain barrier efficiently whereas highly lipophilic molecules strongly bind to plasma lipid-like constituents and cell membranes. Consequently, only a small fraction of the ligand in plasma is free and able to cross the blood-brain barrier. In concordance with this explanation is the observation that N-fluoroethyl substituted benzamides (47), which are very lipophilic (log $k_W$ greater than 3.6, D. Schmidt, unpublished observation), have high plasma binding.

The following conclusions may be drawn from this example. First, the new iodobenzamide derivatives studies, i.e., epidepride and ioxipride, appear to be superior candidates as SPECT ligands for study of the D2 receptor. Second, not only high affinity but also relatively low lipophilicity range, corresponding to low $k_W$ =1.7 to 3.3, is required for reasonable brain uptake. Thus ligands with a log $k_W$ 1.7 to 2.5 and a $K_D$ of 0.1 nM or less, should have optimal affinity and lipophilicity for imaging.

EXAMPLE 7

This example shows imaging methods in accordance with the present invention in primates.

Four 8–10 kg male rhesus monkeys were studied on five separate occasions. All received 10 mg/kg ketamine intramuscularly, were intubated and a surgical level of inhalation anaesthesia was maintained with 0.8 to 1.2% halothane for the duration of the study. No muscle relaxants were used during these studies. After inhalational anaesthesia was established, an intravenous catheter was placed for administration of the radiolabelled tracer and a femoral arterial catheter was placed for arterial blood sampling. Four to 10 mCi of [$^{123}$I]epidepride was administered intravenously. All studies were performed using a Siemens ZLC rotating gamma camera with a high resolution, low energy collimator. For the initial 10 minutes following injection, multiple lateral planar images of the head with a frame duration of 10 seconds/frame were obtained. Immediately following these planar images, serial tomographic images were obtained using 65 views, with 7 to 10 seconds per view for periods of up to 10 hours after injection.

Plots of striatal radioactivity, posterior brain radioactivity (a region with low levels of dopamine receptors), and striatal:posterior brain ratios are shown in FIG. 15. Striatal uptake peaked at 0.58% of injected dose at 83 minutes after injection. Activity then declined to a relatively stable level between 0.23 and 0.14% of injected dose between 2.1 and 6.4 hours after injection. The half-life of washout was 6 hours for total striatal uptake and 7.5 hours for striatal minus posterior brain uptake. Uptake in the posterior brain region peaked at 40 minutes after injection, then declined to the end of the study with a half-life of washout of 65 minutes. At 25 minutes after injection the striatal:posterior brain ration was 2. This increased to 6.8 at 105 minutes after injection, to 15 at 4.1 hours and to 58 at 6.4 hours following injection. Thus, combination of stable striatal radioactivity and declining posterior brain radioactivity lead to increasing ratios of striatum:posterior brain radioactivity.

To examine the reversibility of binding in vivo in primates, [$^{123}$I]epidepride was administered intravenously and striatal levels of radioactivity were allowed to reach a relatively stable level. At 2.5 hours after injection haloperidol was administered intravenously during two studies, once at a dose of 0.1 mg/kg (FIG. 16) and once at a dose of 1 mg/kg. In both cases a monoexponential washout of radioactivity was observed, with half-lives of 59 and 53 minutes, respectively. Thus, the in vivo striatal uptake of [$^{123}$I] epidepride is reversible in vivo in primates. The uptake evident within the orbit (FIG. 16) was not displaceable by haloperidol. Post mortem dissection of one monkey revealed that most orbital radioactivity was in orbital fat and not in the globe.

The effect of d-amphetamine, at doses of 1 and 2 mg/kg intravenously, on striatal uptake of [$^{123}$I]epidepride was studied to ascertain the effect of endogenous dopamine. [$^{123}$I]Epidepride was administered and the striatal uptake was allowed to reach a stable level. Amphetamine was administered in two separate experiments and scans were obtained for up to 60 minutes following amphetamine administration. At a dose of 2 mg/kg some amphetamine-induced motor movement occurred, but less than 10% of striatal epidepride was displaced over 70 minutes post-amphetamine period.

The data from the 1 mg/kg d-amphetamine experiment is shown in FIG. 17. The theoretical curve is determined by least squares fit of the equation y=a*exp(-b*t) to the 5 data points preceding d-amphetamine injection. The fit parameters are a=19±2 nCi and b=0.0019±0.0007 min$^{-1}$. Assuming that the variance of all data are equal, the sample variance from the expected value is v=1.37 nCi. This assumption is not strictly valid because the variance will increase as the activity decreases. However, the increase in variance due to counting statistics within the region of interest cannot be known and probably is small Compared to the above value. The n=2 post data points have an average deviation for the expected value of μ=0.15 nCi with a standard error of v/√(n)=0.969 nCi. The area under the normal curve, P(x), with |x|>μ gives the probability that two random samples drawn from the pre-amphetamine distribution will have an average deviation greater than μ. The probability is 88%. Therefore, the null hypothesis cannot be disproved implying that the amphetamine injection had no significant effect on the uptake. Alternatively, one could ask what is the smallest amphetamine induced displacement that could be detected with 90% confidence. Calculating in a similar fashion to the above, we find that a 2.2 nCi or greater divergence from the expected value of 11.0 nCi (corresponding to a 20% displacement in the last data point) may be attributed to an amphetamine induced effect with 90% confidence. Therefore, the measured deviation of 0.9 nCi (8% change from the expected value) is most likely due to random variance in the data alone.

EXAMPLE 8

This example shows extrastriatal dopamine D2 receptors visualized using [$^{123}$I]epidepride with a high sensitivity, high resolution single photon tomograph and to correlate these results with equilibrium, saturation receptor binding studies of post mortem human brain.

METHODS

Post-Mortem Dissections

Six subjects were examined and had no history of previous neurological disease or psychiatric disease. Up to 23 regions were dissected.

Receptor Binding Studies

Tissue was stored at −80° C. On the day of assay each region was homogenized, using a Brinkman Polytron PT3000 (15,000 RPM for 15 seconds), in a 100 fold (w:v) dilution of a 50 mM Tris HCl buffer, pH 7.4 containing 120 mM NaCl, 5 mM Kcl, 2 mM CaCl$_2$, 1 mM MgCl$_2$, 1 mM Na EDTA and 0.1 mM ascorbic acid. The homogenate was centrifuged at 12,000 x g for 15 minutes at 4° C., resuspended in the same volume of buffer, recentrifuged, and resuspended in buffer at 500 dilution (w:v) for the putamen and 100 (w:v) dilution for the limbic regions. To start the incubation, 0.5 ml of tissue homogenate was added to ice cold assay tubes containing appropriate concentration of radioligand in a final volume of 2 ml. Following addition of tissue, the tubes were removed from ice, vortexed for 3–5 seconds, and incubated at 25° C. for 240 minutes. Incubation was terminated by filtration through Whatman GF/B filters presoaked in 0.3% polyethylinimide, using a Brandel model M-24R cell harvester. The filters were rinsed for 10 seconds with ice cold Tris HC1 buffer and the filter placed in a gamma counting tube. Gamma spectrometry was performed with an LKB model 1282 Universal Compugamma CS instrument. Non-specific binding was determined using 10 mM (final conc) sulpiride. To determine the IC50's for displacement of [$^{125}$I]epidepride from striatal and extrastriatal regions by binding of [$^{125}$I]epidepride (50 pM final conc) at eleven different concentrations (0–100,000 nM) of these ligands were measured in duplicate.

Single Photon Tomographic Imaging With [$^{123}$I]Epidepride

A 27 year old normal male volunteer was administered 5 mCi [$^{123}$I]epidepride intravenously and starting at five minutes post injection, four sequential 15 minute image acquisitions were obtained. An additional 40 minute image acquisition was obtained at 3.7 to 4.3, 18.3 to 19.3 hours and 23.7 to 24.7 hours. All imaging was performed using a TRIAD three-headed single photon tomographic system using a high resolution collimator.

RESULTS

Imaging Studies

Time activity curves of regional brain uptake and representative images are shown in FIGS. 18 and 19. There is rapid uptake of [$^{123}$I]epidepride into the striatum, thalamus, hypothalamus-pituitary regions and temporal cortex, particularly the medial temporal cortex. Uptake in putamen was relatively rapid with levels reaching 88% of peak uptake by 45 minutes after injection; the peak level was seen in the putamen four .hours after injection and declined slowly thereafter so that at eighteen hours after injection levels in the putamen were 46% of that seen at four hours. Uptake in cerebellum reached a peak level i=on the initial scan following injection (12.5 minutes post-injection) and declined thereafter reaching 57% of the initial value 60 minutes later and 34% at 4 hours. As a consequence of the relatively stable uptake in putamen and declining cerebellar levels of radioactivity, the striatal:cerebellar ratio rose from 1.9:1 at 12.5 minutes after injection, to 7.8:1 at 4 hours after injection, to over 400:1 at eighteen hours after injection.

Uptake above the levels seen in cerebellum were observed in the pituitary-hypothalamic region, thalamus and temporal lobe, particularly the medial temporal lobe. Uptake in the thalamus peaked at 45–60 minutes after injection, fell by only 10% at four hours post-injection and declined to low levels at eighteen hours after injection. The ration of thalamic:cerebellar uptake was 2:1 at 45 minutes following injection, 3.75:1 at four hours following injection, and 9:1 at 18 hours after injection. By 18 hours after injection the level of uptake in the thalamus was extremely low. Uptake in the medial temporal lobe and hypothalamus-pituitary regions rose rapidly and reached peak levels at 15–030 minutes post-injection: uptake in these structures fell to about half the peak values by 4 hours and fell to very low levels but remained above background at 18 and 24 hours after injection. The medial temporal:cerebellar and hypothalamic-pituitary:cerebellar rations were 2.0:1 and 1.7:1 at 45 minutes, and rose to 2.3:1 for both regions at four hours. In the frontal cortex, ratios ranged between 1.13 and 1.39 at times up to four hours. $^{125}$I]Epidepride Binding in Post-Mortem Human Brain Scatchard analysis of saturation equilibrium binding studies was performed in twenty-three regions of human brain (See Table 9). As in previous post-mortem studies of human brain, the highest levels of [$^{125}$I]epidepride binding were seen in the caudate (16.5 pmoles/g tissue) and putamen (16.6 pmoles/g tissue) followed by the globus pallidus (7.0 pmoles/g tissue) and nucleus accumbens (7.2 pmoles/g tissue). Of the structures often described as being a part of the limbic system (13,14), intermediate to low levels of binding were seen; the hypothalamus had the highest concentration, 1.8 pmoles/g tissue, followed by the substantia innominate (1.0) and amygdala (0.87). Lower levels were seen in the uncal cortex (0.44), anterior hippocampus (0.36), parahippocampal gyrus (0.31), anterior perforated substance (0.27) and anterior congulate (0.26). Of note were very low levels of binding sites in several regions of the frontal lobe. Of the three regions examined, orbitofrontal cortex, middle frontal gyrus and medial frontal lobe, all had densities ranging from 0.17 to 0.20 pmole/g tissue. Uncal (0.46) and inferior temporal frontal cortex (0.44) have receptor densities approximately twice that seen in the frontal lobe regions. The lateral temporal cortex (0.28) also demonstrates densities higher than that noted in the frontal cortex.

Of considerable note is the presence of significant numbers of D2 receptors in the thalamus. Densities of 1.0, 0.96, 0.72 and 0.86 pmole/g tissue were seen in the anterior nucleus, dorsomedial nucleus, ventral nuclei and pulvinar respectively. These values are comparable to that seen in the amygdala and substantia innominate and 2 to 5 times higher than those seen in temporal and frontal cortex.

Specificity of Binding in Human Brain

Competitive displacement of [$^{125}$I]epidepride by noradrenergic, muscarinic cholinergic, GABAergic, opiate, sigma, serotonergic and dopamine D1 receptor ligands revealed a low to very low affinity of these ligands for the [$^{125}$I]epidepride binding site in putamen, ventral nucleus of thalamus and inferior temporal cortex. Similar findings were also seen in the hypothalamus and nucleus accumbens. Only dopamine D2 ligands demonstrated high to very high affinity for the [$^{125}$I]epidepride binding site in the regions examined. There is a very correlation (r=0.995) between the IC$_{50}$'s for inhibition of [$^3$H]spiperone and [$^{125}$I]epidepride by a variety of dopamine D2 ligands using homogenates of putamen, indicating that [$^{125}$I]epidepride binds to a D2 site in the putamen. A similar correlation was attempted using uncal cortex. The K$_i$'s for inhibition of [$^{125}$I]epidepride binding are shown in Table 10. No specific [$^3$H]spiperone binding could be identified in uncal cortex; serotonergic binding was inhibited by including ketanserin (1 μM) in the incubation mixture. The K$_i$'s for [$^{125}$I]epidepride correlate closely with published K$_D$'s of these ligands for the dopamine D2 receptor indicating that [$^{125}$I]epidepride appears to bind to a dopamine D2 site in uncal cortex.

This example demonstrates that radiolabelled epidepride can be used to study striatal and extrastriatal dopamine D2 receptors in man in vivo with high resolution single photon tomography and in vitro using post mortem brain tissue. High levels of binding was seen in vitro in the basal ganglia and nucleus accumbens while lower levels of uptake were seen in the amygdala, hypothalamus and medial temporal lobe. In vivo uptake seen in the [$^{125}$I]epidepride imaging study paralleled the in vitro [$^{125}$I]epidepride binding studies with highest uptake seen in the basal ganglia and lower levels seen in the thalamus, hypothalamus and temporal lobe. Previous positron tomographic studies of D2 receptors using [$^{11}$C]raclopride(2) and [$^{11}$C]N-methylspiperone(19) have failed to report thalamic or temporal lobe uptake. The uptake seen in the thalamus on emission tomography with [$^{123}$I]epidepride was higher than in other extrastriatal regions where autopsy studies demonstrated a higher density of [$^{125}$I]epidepride binding sites.

In conclusion, this study demonstrates that radiolabelled epidepride can be used to study human extrastriatal as well as striatal dopamine D2 receptors both in vivo and in vitro. The distribution of dopamine D2 receptors in human brain has been demonstrated to be significantly different than that reported in rats and monkeys. Of particular note are the moderate levels of D2 receptors in the thalamus and the low levels seen in frontal cortex.

This invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

What is claimed is:

1. A method of radioimaging a human brain comprising the steps of:

systemically administering an effective amount of a radio-iodinated substituted benzamide to a patient, the benzamide having the formula:

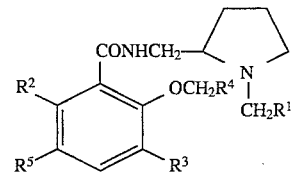

wherein R$^5$ is $^{123}$I, $^{125}$I, or $^{131}$I, and R$^1$ is a hydrogen atom, a lower alkyl group consisting of 1–4 carbon atoms, a cycloalkyl group consisting of 3–6 carbon atoms, an alkenyl group which contains 2–4 carbon atoms, or an alkynyl group consisting of 2–4 carbon atoms; R$^2$ is a hydrogen atom or a hydroxyl group; R$^3$ is a hydrogen atom, a chlorine atom, a methoxy group, or a methyl group, and R$^4$ is a hydrogen atom, or a methyl group, and wherein R$^3$ and R$^4$ are not both hydrogen when R$^2$ is a hydroxyl such that said administration results in uptake levels of the substituted benzamide in dopamine D2 receptor poor regions which are relatively lower than uptake levels of the substituted benzamide in dopamine D2 receptor rich regions;

detecting gamma radiation emitted by said composition; and forming a high contrast image therefrom.

2. A method as set forth in claim 1 wherein the substituted benzamide has a lipophilicity range corresponding from about log k$_W$=1.7 to 3.3 at pH 7.5.

3. A method as set forth in claim 2 wherein the substituted benzamide has a lipophilicity range corresponding from log k$_W$=1.7 to 2.8 at pH 7.5 and a K$_D$ of 0.15 nM or less.

4. A radioimaging compound selected from the group consisting of radioiodinated substituted benzamide wherein the substituted benzamide has a lipophilicity range from about log k$_W$=1.7 to 3.3 at pH 7.5 and a K$_D$ of about 0.15 nM or less having the formula:

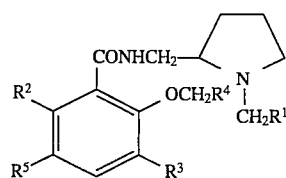

wherein $R^5$ is $^{123}I$, $^{125}I$, or $^{131}I$, and $R^1$ is a hydrogen atom, a lower alkyl group consisting of 1–4 carbon atoms, a cycloalkyl group consisting of 3–6 carbon atoms, an alkenyl group which contains 2–4 carbon atoms, or an alkynyl group consisting of 2–4 carbon atoms; $R^2$ is a hydrogen atom or a hydroxyl group; $R^3$ is a hydrogen atom, a chlorine atom, a methoxy group, or a methyl group, and $R^4$ is a hydrogen atom or a methyl group, wherein $R^3$ and $R^4$ are not both hydrogen when $R^2$ is a hydroxyl.

5. A pharmaceutical composition comprising:
a radioimaging compound selected from the group consisting of radioiodinated substituted benzamide having a lipophilicity range from about log $k_W$=1.7 to 3.3 at pH 7.5 and a $K_D$ of about 0.15 nM or less; and a liquid carrier having the formula:

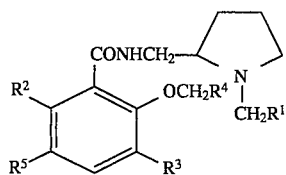

wherein $R^5$ is $^{123}I$, $^{125}I$ or $^{131}I$ and $R^1$ is a hydrogen atom, a lower alkyl group consisting of 1–4 carbon atoms, a cycloalkyl group consisting of 3–6 carbon atoms, an alkenyl group which contains 2–4 carbon atoms, or an group consisting of 2–4 carbon atoms; $R^2$ is a hydrogen atom or a hydroxyl group; $R^3$ is a hydrogen atom, a chlorine atom, a methoxy group, or a methyl group, and R4 is a hydrogen atom or a methyl group, wherein $R^3$ and $R^4$ are not both hydrogen when $R^2$ is a hydroxyl.

6. A composition as set forth in claim 5 wherein said carrier is physiological saline.

7. A composition as set forth in claim 5 including about 2 to 20 mCi of $^{123}I$-labelled substituted benzamide.

8. A method of radioimaging a human brain comprising the steps of:

systemically administering an effective amount of a radioiodinated substituted benzamide to a patient, the benzamide being selected from the group consisting essentially of (S)-N-5-iodo-2-methoxybenzamide; (S)-(N)-3-iodo-5-methoxy-6 ethoxysalicylamide; (S)-(N)-3-iodo-5,6-dimethoxy-salicylamide; (S)-N-5-iodo-2-ethoxy-3-methoxybenzamide; and (S)-N-5-iodo-2,3-dimethoxy-benzamide such that said administration results in uptake levels of the substituted benzamide in dopamine D2 receptor poor regions which are relatiely lower than uptake levels of the substituted benzamide in dopamine D2 receptor rich regions;

detecting gamm radiation emitted by said benzamide; and forming a high contrast image therefrom.

* * * * *